(12) United States Patent
Zhang et al.

(10) Patent No.: US 8,321,003 B2
(45) Date of Patent: Nov. 27, 2012

(54) METHODS AND APPARATUSES FOR DETECTION OF MYOCARDIAL ISCHEMIA UPON EXERTION

(75) Inventors: Yi Zhang, Plymouth, MN (US);
Kenneth C. Beck, St. Paul, MN (US);
Aaron Lewicke, Forest Lake, MN (US);
Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 600 days.

(21) Appl. No.: 12/508,398

(22) Filed: Jul. 23, 2009

(65) Prior Publication Data

US 2010/0030090 A1 Feb. 4, 2010

Related U.S. Application Data

(60) Provisional application No. 61/137,727, filed on Aug. 1, 2008.

(51) Int. Cl.
*A61B 5/04* (2006.01)
(52) U.S. Cl. ........................................ 600/513; 600/509
(58) Field of Classification Search .................. 600/513, 600/509
See application file for complete search history.

(56) References Cited

U.S. PATENT DOCUMENTS

| | | | |
|---|---|---|---|
| 6,016,443 A * | 1/2000 | Ekwall et al. ................. | 600/519 |
| 6,264,606 B1 | 7/2001 | Ekwall et al. | |
| 6,368,284 B1 | 4/2002 | Bardy | |
| 7,181,269 B1 | 2/2007 | Kroll | |
| 7,218,960 B1 | 5/2007 | Min et al. | |
| 7,225,015 B1 | 5/2007 | Min et al. | |
| 7,254,440 B1 | 8/2007 | Kroll | |
| 7,274,959 B1 | 9/2007 | Wang et al. | |
| 2005/0113705 A1 | 5/2005 | Fischell et al. | |
| 2007/0021678 A1 | 1/2007 | Beck et al. | |
| 2007/0088400 A1 | 4/2007 | Jacobson | |
| 2007/0093720 A1* | 4/2007 | Fischell et al. ................ | 600/509 |

(Continued)

FOREIGN PATENT DOCUMENTS

WO WO2007/011565 1/2007

OTHER PUBLICATIONS

Zubarev et al., "Rheocardopgraphic Evaluation of Left-Ventricular Contractility in the Measured Isometric Pedal Test", Kardiologiia, vol. 29(2), Feb. 1989, pp. 70-74.

(Continued)

*Primary Examiner* — Carl H Layno
*Assistant Examiner* — Natasha Patel
(74) *Attorney, Agent, or Firm* — Hollingsworth Davis, LLC

(57) ABSTRACT

Various method embodiments of the present invention concern sensing patient-internal pressure measurements indicative of physiological exertion, identifying one or more steady state periods of physiological exertion based on the patient-internal pressure measurements, sensing extra-cardiac response data and cardiac response data corresponding to the one or more physiological exertion steady state periods, respectively comparing the extra-cardiac response data and the cardiac response data to extra-cardiac response information and cardiac response information associated with equivalent levels of physiological exertion intensity of the one or more steady state periods, and determining the likelihood that myocardial ischemia occurred during the one or more steady state periods based on the comparison of the extra-cardiac response data to the extra-cardiac response information and the cardiac response data to the cardiac response information.

28 Claims, 11 Drawing Sheets

U.S. PATENT DOCUMENTS

2009/0143690 A1* 6/2009 Bjorling et al. ............... 600/509
2009/0204167 A1* 8/2009 Bauer ............................ 607/25

OTHER PUBLICATIONS

St. Jude Medical, "2008 Investor Conference", Feb. 8, 2008.
Tanabe et al., "Unstable Angina Pectoris—Changes in the ST-T Segment during Daily Activities such as Bathing, Eating, Defecating and Urinating", Japanese Circulation Journal, vol. 47, Apr. 1983, pp. 451-458.
1975, Singman et al., "Electrocardiographic Changes in Coronary Care Unit Patients During Defecation", Vascular Surgery, Jan.-Feb.; 9(1), pp. 54-57.
Ishizaka et al., "Development of a New Activity-Input-Type Ambulatory Electrocardiogram and its Clinical Usefulness", Japanese Circulation Journal, vol. 55, Apr. 1991, pp. 303-315.

* cited by examiner

| Activity (mg) | iMV | iVT | iRR |
|---|---|---|---|
| 120 | 69.6 | 2.4 | 29 |
| 110 | 55.0 | 2.2 | 25 |
| 100 | 46.2 | 2.1 | 22 |
| 90 | 36.1 | 1.9 | 19 |
| 80 | 30.6 | 1.8 | 17 |
| 70 | 27.2 | 1.7 | 16 |
| 60 | 22.5 | 1.5 | 15 |
| 50 | 21.0 | 1.4 | 15 |
| 40 | 16.8 | 1.2 | 14 |
| 30 | 15.4 | 1.1 | 14 |
| 20 | 11.7 | 0.9 | 13 |
| 10 | 9.8 | 0.7 | 14 |
| 0 | 7.8 | 0.6 | 13 |

Figure 4

| Activity (mg) | ST | FCC | PVC | AF% |
|---|---|---|---|---|
| 120 | 2.10 | 0.81 | 12 | 38 |
| 110 | 1.80 | 0.85 | 8 | 32 |
| 100 | 1.50 | 0.88 | 6 | 25 |
| 90 | 0.80 | 0.92 | 5 | 18 |
| 80 | 0.30 | 0.94 | 5 | 12 |
| 70 | 0.28 | 0.97 | 4 | 4 |
| 60 | 0.25 | 0.97 | 2 | 2 |
| 50 | 0.30 | 0.97 | 0 | 8 |
| 40 | 0.20 | 0.96 | 2 | 3 |
| 30 | 0.15 | 0.98 | 1 | 5 |
| 20 | 0.10 | 0.98 | 0 | 0 |
| 10 | 0.10 | 0.97 | 0 | 0 |
| 0 | 0.10 | 0.97 | 0 | 0 |

Figure 5

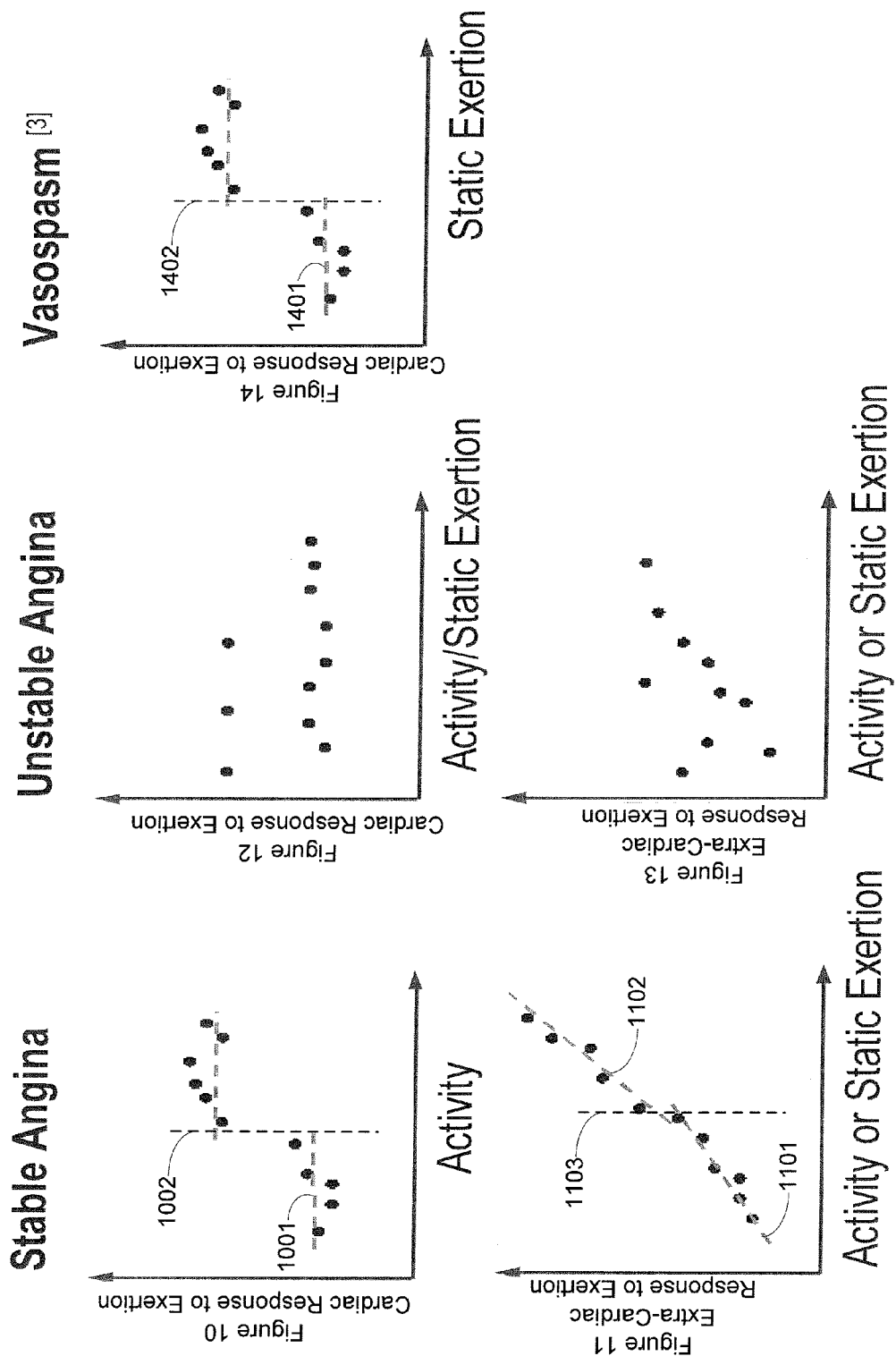

METHODS AND APPARATUSES FOR DETECTION OF MYOCARDIAL ISCHEMIA UPON EXERTION

RELATED APPLICATIONS

This application claims the benefit of Provisional Patent Application Ser. No. 61/137,727, filed on Aug. 1, 2008, to which priority is claimed pursuant to 35 U.S.C. §119(e) and which is hereby incorporated herein by reference.

FIELD OF THE INVENTION

The present invention relates generally to implantable medical devices, and more specifically, to detection of myocardial ischemia during exertion episodes.

BACKGROUND

Ischemia generally refers to a restriction in blood supply. Myocardial ischemia is a type of ischemia characterized by inadequate blood supply to the heart muscle. Generally speaking, two types of myocardial ischemia exist. The first is demand ischemia, which is associated with increased oxygen demand due to increased metabolism in the heart muscle. The second is supply ischemia, which is associated with decreased oxygen supply due to restricted blood flow in the coronary artery. Demand ischemia can happen during times of physical exertion or emotion stress, or even while at rest in severe cases.

Ischemic heart disease may present any number of problems. One such problem is angina pectoris, where myocardial ischemia manifests as chest pain experienced by a person during exertion, in cold weather, during emotional situations, or spontaneously due to coronary vasospasm, among other situations. Refraining from exertion, avoiding cold weather, or calming can sometimes address an episode of chest pain.

Further manifestations of myocardial ischemia include acute chest pain, reduced physical capabilities, unstable angina, and myocardial infarction (heart attack). Myocardial ischemia in such manifestations is often not relieved by removing a stressor or resting the patient. Acute heart damage can also result if the ischemic episode is severe or prolonged enough. Progression of myocardial ischemia can lead to heart failure, which is associated with difficulty in breathing, fatigue, swelling of the extremities due to inadequate circulation, and death.

Several treatment options for myocardial ischemia exist. For example, lifestyle changes, such as cessation of smoking, increasing physical activity, and weight optimization can help limit the progression of myocardial ischemia associated with heart disease. Drugs can also be used to relieve symptoms, such as angina, as well as slow the progression of the disease. Addressing other diseases, such as diabetes, can also improve a patient's heart condition. For example, daily aspirin or beta blocking drugs may slow progression, while nitroglycerin can be used to address specific episodes.

SUMMARY OF THE INVENTION

The present invention is generally directed to systems and methods for monitoring the relationship between myocardial ischemia as detected by an electrocardiogram signal and exertion and providing alerts or directing therapy based on the relationship.

For example, some method embodiments of the invention can include obtaining patient-internal pressure measurements indicative of physiological exertion, identifying periods of steady state physiological exertion based on the patient-internal pressure measurements, and assessing the intensity of physiological exertion for each of the identified steady state periods.

Such methods can further include sensing extra-cardiac response data during identified physiological exertion steady state periods, comparing the extra-cardiac response data corresponding to identified steady state periods of physiological exertion with extra-cardiac response information associated with equivalent intensity, and determining the normalcy of the extra-cardiac response data for each steady state period based on the comparison of the extra-cardiac response data and the extra-cardiac response information.

Methods can include sensing cardiac response data during identified physiological exertion steady state periods, comparing the cardiac response data corresponding to identified steady state periods of physiological exertion with cardiac response information associated with equivalent intensity, and determining the normalcy of the cardiac response data for each steady state period based on the comparison of the cardiac response data and the cardiac response information.

Such methods can further include determining the likelihood that myocardial ischemia occurred during one or more of the identified steady state periods of physiological exertion, wherein: the likelihood of ischemia for the one or more steady state periods is determined to be relatively high if both the extra-cardiac response data and the cardiac response data sensed during the one or more steady state periods are determined to be abnormal; the likelihood of ischemia for the one or more steady state periods is determined to be relatively moderate if only one of the extra-cardiac response data and the cardiac response data sensed during the one or more steady state periods is determined to be abnormal; and the likelihood of ischemia for the one or more steady state periods is determined to be relatively low if neither of the extra-cardiac response data and the cardiac response data sensed during the one or more steady state periods are determined to be abnormal. Steady state periods of ischemia can further be classified as stable angina, unstable angina, or vasospasm.

Some system embodiments include an implantable static exertion sensor configured to output an exertion signal responsive to patient static exertion, the exertion signal containing static exertion data, an implantable cardiac parameter sensor configured to output a cardiac signal responsive to a cardiac parameter, the cardiac signal containing cardiac response data, and an implantable extra-cardiac parameter sensor configured to output an extra-cardiac signal responsive to an extra-cardiac parameter, the extra-cardiac signal containing extra-cardiac response data.

Such system embodiments can further include a processor configured to execute program instructions stored in memory to cause the system to: identify steady state periods of physiological exertion based on the static exertion data and assign one of a plurality of exertion intensity levels to each of the steady state periods; organize the cardiac response data and the extra-cardiac response data according to the assigned exertion intensity levels of the identified steady state periods of physiological exertion during which the cardiac response data and the extra-cardiac response data were respectively output; respectively compare the extra-cardiac response data and the cardiac response data to extra-cardiac response information and cardiac response information associated with equivalent levels of physiological exertion intensity of the steady state periods to which the extra-cardiac response data and the cardiac response data is organized; and determine the likelihood that myocardial ischemia occurred during one or more of the periods based on the comparison of the extra-cardiac response data to the extra-cardiac response information and the cardiac response data to the cardiac response information.

Some method embodiments can include obtaining exertion measurements indicative of physiological exertion; identifying one or more steady state periods of physiological exertion based on the exertion measurements; sensing extra-cardiac response data and cardiac response data corresponding to the one or more steady state periods of physiological exertion; respectively comparing the extra-cardiac response data and the cardiac response data to extra-cardiac response information and cardiac response information associated with equivalent levels of physiological exertion intensity of the one or more steady state periods; and determining the likelihood that myocardial ischemia occurred during the one or more steady state periods based on the comparison of the extra-cardiac response data to the extra-cardiac response information and the cardiac response data to the cardiac response information.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 4 and 5 show example tables of extra-cardiac and cardiac response data over a range of exertion levels in accordance with various embodiments of the present invention;

FIGS. 10-14 show plots of cardiac and extra-cardiac response data over a range of exertion levels in accordance with various embodiments of the present invention;

Figure 1:
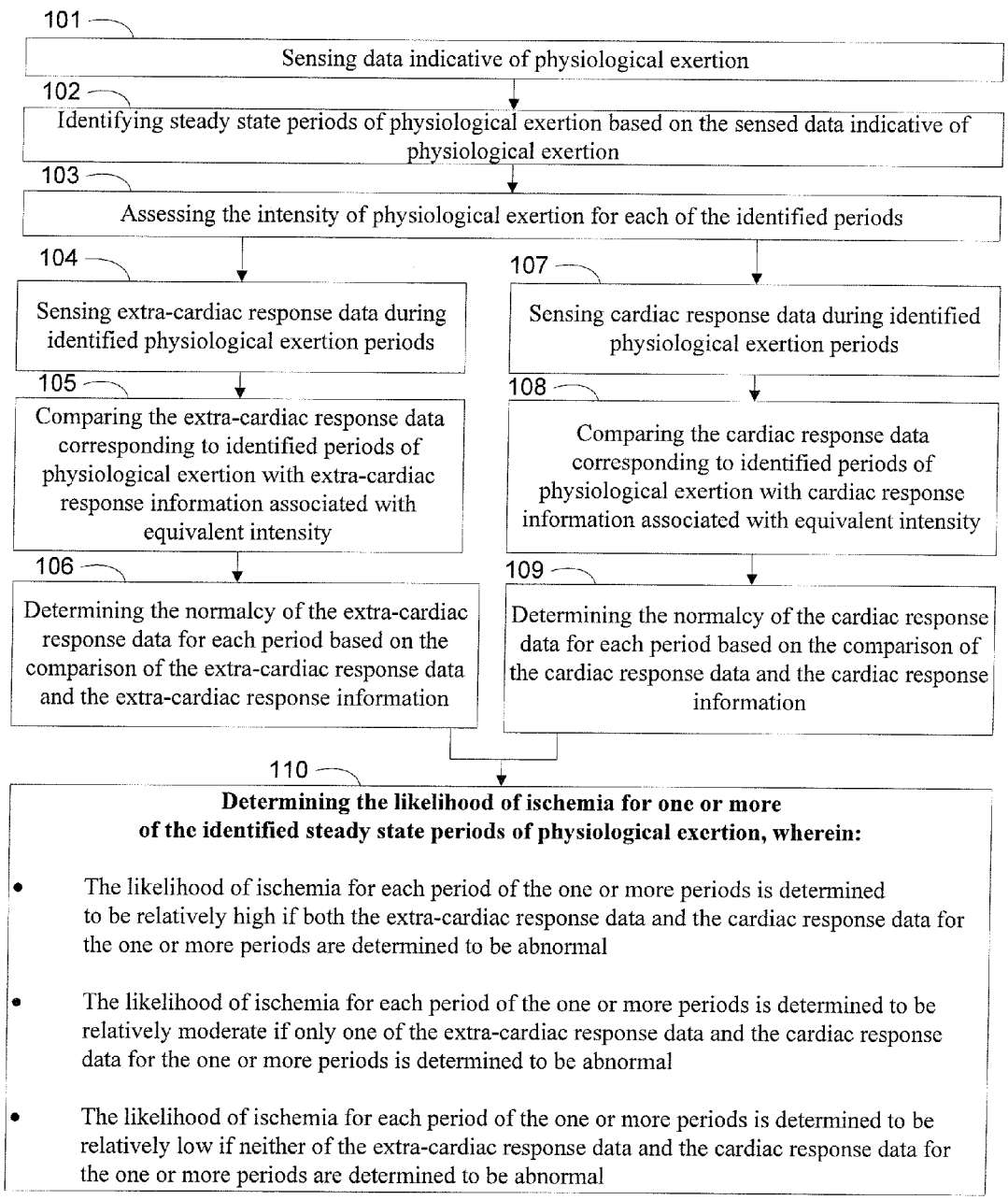
FIG. 1 is a flow diagram showing a method for determining the likelihood of ischemia during identified steady state periods of exertion in accordance with various embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made, without departing from the scope of the present invention.

The discussion and illustrations provided herein are presented in an exemplary format, wherein selected embodiments are described and illustrated to present the various aspects of the present invention. Systems, devices, or methods according to the present invention may include one or more of the features, structures, methods, or combinations thereof described herein. For example, a device or system may be implemented to include one or more of the advantageous features and/or processes described herein. A device or system according to the present invention may be implemented to include multiple features and/or aspects illustrated and/or discussed in separate examples and/or illustrations. It is intended that such a device or system need not include all of the features described herein, but may be implemented to include selected features that provide for useful structures, systems, and/or functionality.

The severity of myocardial ischemia episodes vary widely. In minor cases a patient may not notice an episode of myocardial ischemia or its effects. A patient may experience moderate to severe chest pain (angina), palpitations, breathing difficulty (dyspnea), fatigue, sweating, and nausea in more severe cases of myocardial ischemia.

Myocardial ischemia is often, but not always, associated with physical exertion. For example, a patient may be more likely to experience myocardial ischemia during a period of exertion. Angina correlated with increased physical exertion is associated with stable angina. Physical exertion comes in several forms and varies according to degree. Working in the garden, climbing stairs, walking, shoveling snow, and playing soccer are all forms of physical activity associated with exertion and, for some people, an increased risk of myocardial ischemia. Such activities are forms of dynamic exertion. Dynamic exertion is generally associated with motion of the body caused by voluntary skeletal muscle contraction, and not associated with static increases in internal pressures.

However, a patient does not need to be in motion, or principally using voluntary skeletal muscles, to experience periods of exertion. For example, a patient can experience a period of static exertion during a bowel movement, supporting a weight, or at times of increased emotional stress. Static exertion refers to exertion that is not associated with general limb and body movement. Chest pain when no exertion is present is associated with unstable angina.

A patient may have difficulty in recognizing periods of myocardial ischemia during static exertion and reporting such episodes to a doctor because the patient does not associate stress without vigorous limb movement to be exertion. As such, myocardial ischemia during periods of static exertion can be harder to identify and classify as compared to periods of dynamic exertion, which can complicate the monitoring of myocardial ischemia.

For example, an episode of chest pain may be classified as unstable angina if the patient did not report significant body movement during the episode (or the same was not in some way sensed). But the chest pain may be more accurately identified as stable angina (instead of unstable angina) if it were known that the patient had measurable increased static exertion activity during the episode of chest pain.

Methods and apparatuses are disclosed herein for distinguishing between periods of static and dynamic exertion and detecting myocardial ischemia associated with each.

Static exertion can cause a pressure increase in the thoracic and/or abdominal cavity and spaces. The increase in pressure associated with static exertion can be caused by vigorous, steady contraction of abdominal muscles (e.g., diaphragm) and/or thoracic muscles (e.g., pectorals) against the closed glottis. A monitoring device, such as a patient implantable medical device, can measure and analyze these pressure changes to identify steady state periods of static exertion and characterize cardiac and extra-cardiac responses to static exertion. Static exertion pressure can be measured in the thorax outside of the lungs and blood circulatory system (e.g., one or more pressure implantable sensors located in a non-circulatory location). In some embodiments, a static exertion pressure sensor can be placed in the circulatory system to characterize internal pressure and static exertion level. For example, pulmonary and venous blood pressure can rise with increasing internal pressure due to static exertion, such that sensors in locations proximate the pulmonary and venous blood systems could sense increased static exertion.

Static exertion can also be sensed by strain gauges and/or piezoelectric elements sensing tension in thoracic muscles and/or ligaments and/or other elements of the musculoskeletal system. Static exertion can also be sensed by sensing electromyogram activity of one or more muscles of the thorax or abdomen associated with static exertion (e.g., diaphragm or pectorals).

Dynamic exertion can be assessed by accelerometer, or other type of activity monitor, measurements corresponding to movement of the body (e.g., during walking/running, climbing stairs). The accelerometer or other type of activity monitor can be located in a patient implantable medical device implanted in the pectoral or other region of a patient.

Looking at both static and dynamic exertion classifications can be particularly helpful in detection of myocardial ischemia. For example, a patient may experience a period of exertion that would be not be recorded by an accelerometer alone (e.g., going to the bathroom), and an accelerometer could give false positives (e.g., while traveling in an automobile), or there could be activities that could involve both classifications (e.g., shoveling snow). An accelerometer used with a pressure sensor is particularly useful because it can determine whether an increase in pressure is associated with static exertion (with no corresponding accelerometer increase) or dynamic exertion (with a corresponding increase in accelerometer activity).

Myocardial ischemia detection according to the present invention can be useful for identifying asymptomatic episodes of myocardial ischemia and tracking the progression of heart disease. Myocardial ischemia can progress through several stages. Identification of myocardial ischemia and its stages can help disease diagnosis, identify particular stressors for a patient, and select treatment options. Methods and apparatuses of the present invention can facilitate detection and characterization of myocardial ischemia relative to exertion despite the occurrence of asymptomatic episodes during different types of exertion (e.g., identify exertion-related ischemia, non-exertion-related ischemia, and resting ischemia) and can classify myocardial ischemia as stable myocardial or unstable myocardial ischemia. Methods and embodiments can further facilitate classification of episodes of chest pain (e.g., stable angina, unstable angina, or vasospasm).

Several metrics, and categories of metrics, can be used to assess myocardial ischemia. For example, a patient's extra-cardiac response to exertion can be used as one or more indicators of myocardial ischemia. Metrics of a patient's extra-cardiac response to exertion include, but are not limited to, arterial oxygen saturation, venous oxygen saturation, blood pH level, respiration rate, minute ventilation, core body temperature, pulmonary vascular pressure, and tidal volume. An increase or other change in these metrics can reflect a patient's extra-cardiac response to exertion.

Another category of metrics for assessing a patient's response to exertion concern a patient's cardiac response to exertion. For example, a patient's cardiac response to exertion can include, but is not limited to, heart rate, ST segment (e.g., deviation and/or slope), ECG morphology correlation (such as feature correlation coefficient, FCC, as compared to a saved template), occurrences of premature ventricular contractions (PVC), atrial fibirillation percentage (AF %), QRS complex width (of an electrocardiogram (ECG)), QT interval prolongation, atrial rate, ventricular rate, T-wave amplitude, T-wave polarity, and R wave amplitude of the QRS complex. As shown above, some metrics for evaluating a patient's cardiac response to exertion are electro-cardiac response to exertion parameters and some metrics are non-electro-cardiac response to exertion parameters. Various parameters, such as FCC, are discussed in U.S. Pat. No. 7,319,900, hereby incorporated by reference in its entirety. Because of the number of electro-cardiac metrics usable with the present invention, it may be desirable to use a wideband filter for processing one or more ECG signals.

The methods and systems discussed herein can use either cardiac response to exertion data or extra-cardiac response to exertion data to characterize myocardial ischemia and other conditions. However, various embodiments of the present invention use both of a patient's extra-cardiac response to exertion and cardiac response to the exertion to detect myocardial ischemia. Using both of a patient's extra-cardiac response to exertion and cardiac response to the exertion to detect myocardial ischemia instead of just one of extra-cardiac response to exertion and cardiac response to the exertion provides particular advantages in myocardial ischemia detection and classification of angina, as explained below.

The cardiac response to exertion parameters are sensitive to myocardial ischemia because myocardial ischemia directly affects the heart (e.g., reduced oxygen delivery during periods of myocardial ischemia). Extra-cardiac response parameters may not be directly influenced by myocardial ischemia because myocardial ischemia may not directly affect extra-cardiac organs. For example, oxygen availability to the diaphragm is not necessarily compromised by an episode of myocardial ischemia (however this could happen in severe cases of heart failure leading to death). However, extra-cardiac response parameters may nevertheless be sensitive to myocardial ischemia. For example, myocardial ischemia can lead to reduced cardiac contractile function and pumping efficiency, which can cause a reduction in cardiac output. Reduction in cardiac output can lead to a reduction in oxygen delivery to different organs sufficient to affect operation of those organs. Reduced blood flow in the pulmonary system can limit blood gas exchange in the lungs, leading to lower oxygen and higher carbon dioxide levels in the blood. Higher carbon dioxide blood levels can cause the nervous system to increase breathing intensity (e.g., faster breathing). In this way, the reduction in oxygen delivery associated with myocardial ischemia can be manifested as elevated respiration, shortness of breath, and/or gasping for more air. In addition, myocardial ischemia is known to trigger certain reflexes, principally via the vagus nerve, that stimulate breathing efforts.

In some circumstances, a reduction in cardiac output associated with myocardial ischemia may not be accurately sensed by cardiac parameters, but may nevertheless be detectable by monitoring extra-cardiac parameters. For this and other reasons, myocardial ischemia may affect cardiac response parameters, but not extra-cardiac response parameters in some cases, and affect extra-cardiac response parameters and not cardiac response parameters in some other cases.

As discussed above, a period of myocardial ischemia can affect extra-cardiac response parameters and cardiac response parameters through different mechanisms (e.g., affecting cardiac response to exertion parameters directly and affecting extra-cardiac response to exertion parameters indirectly through the nervous system). According to embodiments of the present invention, an investigation into both extra-cardiac response and cardiac response parameters, and a comparison between them, can provide information and identify trends in a manner that multiple extra-cardiac response parameters, or cardiac response parameters, would not. Moreover, comparison of the normality between extra-cardiac response and cardiac response parameters provides enhanced myocardial ischemia detection and characterization compared to mere independent investigation into extra-cardiac response and cardiac response parameters.

A comparison of extra-cardiac response and cardiac response parameters according to embodiments of the present invention can therefore evaluate the different transitory signatures of myocardial ischemia to provide a way of detecting myocardial ischemia with greater confidence than measuring other collections of exertion response parameters. Moreover, combining the cardiac and extra-cardiac responses would help enhance the positive predictive value of the detection, i.e. reduce false alarms.

FIG. 1 illustrates a method 100 for detecting myocardial ischemia during exertion according to various embodiments of the invention. The method 100 includes sensing 101 data indicative of physiological exertion. The sensed 101 data indicative of physiological exertion can include patient-internal pressure data as a measure of static exertion and/or accelerometer data as a measure of dynamic exertion. Steady state periods of physiological exertion are then identified 102 based on the sensed data indicative of physiological exertion.

In some embodiments of the invention, steady state periods of physiological exertion are identified by sustained periods during which a metric tracking exertion indicates a signature of exertion. For example, if patient-internal pressure is the parameter indicative of physiological exertion, then any period of three seconds or more of increased internal pressure can be identified as a steady state period of physiological exertion. If an accelerometer is used, then relatively longer periods (e.g., sustained for 20 seconds) of elevated acceleration indicated activity may be used to identify steady state periods. Requiring longer sustained periods of accelerometer activity to identify steady state periods of physiological exertion can help avoid misidentification of transitional activity, such as sitting down or rolling to one's side, as a steady state period of dynamic exertion.

Each of the identified 102 steady state periods of physiological exertion can be assessed 103 to determine the intensity of physiological exertion for each steady state period. For example, a metric range (e.g., internal pressure of the pleural cavity) can be established with various sub-ranges (e.g., 0-10 mmHg, 10-20 mmHg, 20-30 mmHg, etc). The intensity for a particular steady state period can be assessed based on the maximum parameter value measured during the steady state period, the minimum parameter value measured during the steady state period, or the average parameter value during the steady state period, for example. Assessing the intensity of physiological exertion during a steady state period can include categorizing the steady state period amongst the sub-ranges into which the assessed intensities fit. For example, if the average pressure for a steady state period of exertion is 21 mmHg, then the steady state period could be classified within a 20-29 mmHg sub-range. In this manner, data can be categorized into various bins corresponding to sub-ranges as it is collected. United States Patent Application No. 20070021678, herein incorporated by reference in its entirety, demonstrates how steady state periods can be identified and data organized in bins.

The method 100 illustrates two parallel tracks (104-105-106 and 107-108-109) which both span steps 103 and 110. It is possible that of the two tracks, only track 104-105-106 would be performed, or that only track 107-108-109 would be performed. However, both tracks are performed in preferred embodiments of the invention. As discussed herein, there are particular synergistic advantages for performing both tracks that enhance ischemia detection and classification beyond performing just one of the tracks. The steps of tracks 104-105-106 and 107-108-109 can be performed simultaneously, sequentially, or in a non-sequential order.

Track 104-105-106 includes sensing 104 extra-cardiac response data during identified physiological exertion steady state periods. Sensing 104 extra-cardiac response data can include sensing data of a single parameter, such as tidal volume, or multiple parameters, such as minute ventilation and breathing rate, among other extra-cardiac response parameters and combinations.

The sensed 104 extra-cardiac response data is then compared 105 to extra-cardiac response information. This step compares 105 extra-cardiac response data corresponding to (e.g., taken during) identified 102 steady state periods of physiological exertion with extra-cardiac response information associated with equivalent physiological exertion intensity. As such, the level at which the intensity is assessed 103 for a particular steady state period can determine to which extra-cardiac response information the sensed 104 extra-cardiac response data is compared.

For example, if the assessed 103 intensity level for a particular steady state period determines that the physiological exertion data averages 15 mmHg during a steady state period, and categorizes the steady state period in a 10-20 mmHg sub-range, then extra-cardiac response data sensed 104 during that steady state period may be compared 105 with extra-cardiac response information associated with a particular steady state period collected during a previous steady state period of exertion associated with the 10-20 mmHg sub-range.

Making comparisons in this manner allows a patient's extra-cardiac response data to be compared to extra-cardiac response information associated with exertions of equivalent intensity, for example. This facilitates an apples-to-apples comparison, as extra-cardiac response data of relatively minor exertions can be compared to previously collected extra-cardiac response data of relatively minor exertions, extra-cardiac response data of more moderate exertions can be compared to previously collected extra-cardiac response data of relatively more moderate exertions, data of higher level exertions to data of higher level exertions, and so on. Comparison in this manner allows a patient's response to exertion to be tracked for each of a plurality of exertion levels, such that response changes that occur at some levels (e.g., PVC rate only increases over time at moderate levels of exertion) can still be tracked. These concepts apply in the method steps concerning electro-physiological response to exertion as well.

The method 100 further includes determining 106 the normalcy of the extra-cardiac response data for each steady state period based on the comparison of the extra-cardiac response data and the extra-cardiac response information. How this step is performed can vary depending on the nature of the extra-cardiac response information. The extra-cardiac response information may be recognized personal trends, recognized population trends, thresholds, baselines, and/or ranges, among other types of information.

For example, the sensed 104 extra-cardiac response information may be respiration rate, and the extra-cardiac response information may be a respiration rate baseline for a particular level of intensity. The comparison 105 may compare the respiration rate of a steady state period with a particular level of intensity to a baseline respiration rate for that particular level of intensity. It may be determined 106 that the respiration rate deviates from the baseline based on the comparison 105 to such a degree that the extra-cardiac response is abnormal, as least according to the extra-cardiac response data for an intensity level of exertion for the steady state period. Other types of comparisons and determinations of normalcy of exertion response as discussed herein are contemplated for such methods. In some embodiments, cardiac or extra-cardiac to response data is abnormal if it does not follow a linear trend of increasing in intensity with increasing physiological exertion (e.g., the response is erratic or unexpectantly high across exertion intensity levels).

Turning to track 107-108-109, cardiac response data can be sensed 107 during identified physiological exertion steady state periods. Sensing 107 cardiac response data can include sensing a patient's ECG, which can include parameters such as ST segment deviation and QRS complex width, among others.

The sensed 107 cardiac response data is then compared 108 to cardiac response information. This step compares 108 cardiac response data corresponding to (e.g., taken during) identified 102 steady state periods of physiological exertion with cardiac response information associated with equivalent intensity. As such, the level at which the intensity is assessed 103 for a particular steady state period can determine which cardiac response information the sensed 107 cardiac response data is compared to. For example, if the assessed 103 intensity level for a particular steady state period determines that the physiological exertion data averages 5 mmHg during an steady state period, and categorizes the steady state period in a 5-10 mmHg sub-range, then cardiac response data sensed 107 during that steady state period may be compared 108 with cardiac response information associated with a previous steady state period of exertion associated with the 5-10 mmHg sub-range. Making comparisons in this manner allows a patient's cardiac response to exertion to be compared to response information associated with exertions of equivalent intensity, for example. This facilitates an apples-to-apples comparison, as cardiac responses of relatively minor exertions can be compared to previous cardiac responses of relatively minor exertions, cardiac responses of more moderate exertions can be compared to previous cardiac responses of relatively more moderate exertions, data of higher level exertions to data of previous higher level exertions, and so on.

The method 100 further includes determining 109 the normalcy of the cardiac response data for each steady state period based on the comparison of the cardiac response data and the cardiac response information. How this step is performed can vary depending on the nature of the cardiac response information. The cardiac response information may be recognized personal trends, recognized population trends, thresholds, baselines, and/or ranges, among other types of information.

For example, the sensed 107 cardiac response information may be the number or rate of premature ventricular contractions, and the cardiac response to exertion information may be a baseline number or rate of premature ventricular contractions for a particular level of intensity. The comparison 108 may compare the premature ventricular contraction rate of a steady state period with a particular level of intensity to a baseline premature ventricular contraction rate for that particular level of intensity. It may be determined 109 that the premature ventricular contraction rate deviates from the baseline based on the comparison 107 to such a degree that the cardiac response to exertion during the steady state period is abnormal. Other types of comparisons and determinations of normalcy of exertion response as discussed herein are contemplated for such methods.

Based on the determinations 106 and 109 of normalcy of the extra-cardiac and cardiac response data, the likelihood of ischemia can be determined 110. The likelihood of ischemia for a steady state period may be determined 110 to be relatively high if both the extra-cardiac response data and the cardiac response data for the one or more steady state periods are determined 106 and 109 to be abnormal. The likelihood of ischemia for a steady state period may be determined 110 to be relatively moderate if only one of the extra-cardiac response data and the cardiac response data is determined 106 and 109 to be abnormal. The likelihood of ischemia for a steady state period may be determined 110 to be relatively low if neither of the extra-cardiac response data and the cardiac response data are determined 106 and 109 to be abnormal.

Figure 2:
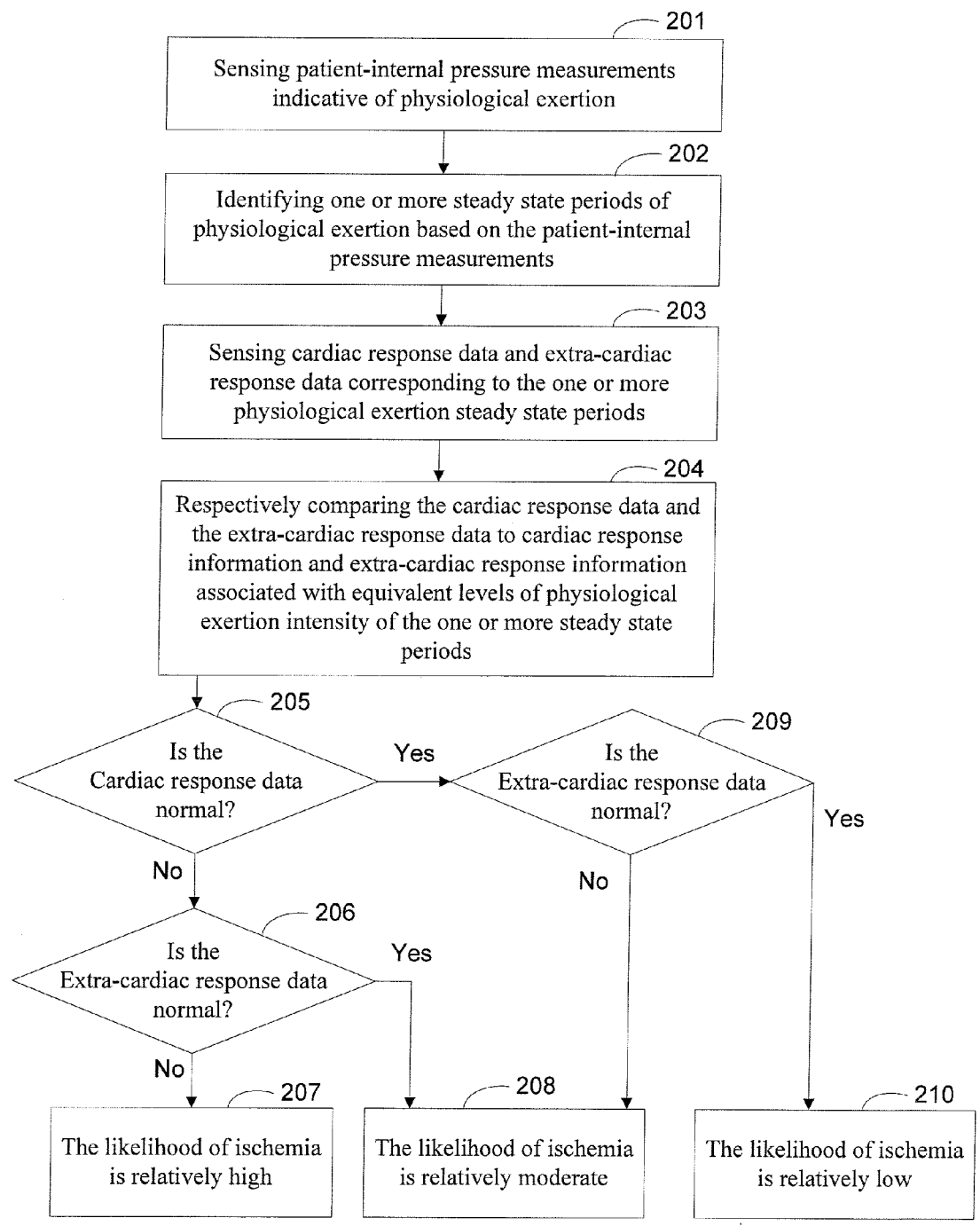
FIG. 2 is a flow diagram showing a method for determining the likelihood of ischemia during identified steady state periods of exertion in accordance with various embodiments of the present invention.

FIG. 2 illustrates a method 200 for detecting myocardial ischemia during exertion according to various embodiments of the invention. The method 200 includes sensing 201 patient-internal pressure measurements indicative of physiological exertion. The method further includes identifying 202 one or more steady state periods of physiological exertion based on the sensed 201 patient-internal pressure measurements. The identification of a steady state period can be based on a rise in patient-internal pressure or a sustained period of increased pressure. Corresponding to the one or more identified 202 steady state periods, extra-cardiac response data and cardiac response data can be sensed 203.

In some embodiments, pressure, extra-cardiac response data, and/or cardiac response data is sensed and recorded continuously. This data can be temporarily recorded on a first-in-first-out buffer, wherein the data is eventually replaced if a steady state period of exertion is not detected, or the data is stored (moved to memory) in a more permanent manner when a steady state period of exertion is detection. Therefore, in case the steady state period of exertion is not identified 202 until the steady state period has already begun, or has already concluded, the sensed 203 extra-cardiac response data and the cardiac response data corresponding to the steady state period (e.g., starting at the beginning of the steady state period and continuing to the end of the steady state period) can still be accessed.

The method 200 further includes respectively comparing 204 the extra-cardiac response data and the cardiac response data to extra-cardiac response information and cardiac response information associated with equivalent levels of physiological exertion intensity of the one or more steady state periods. In this way, the extra-cardiac response data of a particular steady state period of exertion will be compared to extra-cardiac response information associated with a level of exertion intensity equivalent to the intensity level of the steady state period. Also, the cardiac response data of a particular steady state period of exertion will be compared to cardiac response information associated with a level of exertion intensity equivalent to the intensity level of the steady state period.

Comparing 204 the extra-cardiac response information and cardiac response information along levels of exertion allows for a deeper level of investigation into a patient's response to exertion and enhanced pattern recognition. For example, while it may be the case that a patient's overall respiration rate response to exertion changes over time, it may be important to know that the respiration rate has only changed for moderate and high levels of exertion as compared to previous exertion steady state periods, while the respiration rate for low exertion remains unexpectedly unchanged. Knowing the spectrum along levels of exertion of changes over time in a patient's cardiac and extra-cardiac response to exertion can allow greater understanding of a patient's myocardial ischemia progression. Furthermore, knowing which particular levels of exertion can lead to dangerous conditions can provide more accurate warnings to patient/physician and/or therapy adjustment.

The method 200 further includes determining 205 if the cardiac response data is normal. Such a determination can be made using the comparison 204 of the cardiac response data to the cardiac response information associated with equivalent levels of physiological exertion of the one or more steady state periods. Normalcy can be determined by identifying deviations in the cardiac response data from that of one or more previous steady state periods, a baseline, a threshold, a pattern, or a trend, among other things. If the cardiac response data is determined 205 to be normal, then the method 200 moves to step 209. If the cardiac response data is not determined 205 to be normal, then the method 200 moves to step 206.

Depending on the outcome of step 206, it may be determined 206 whether the extra-cardiac response data is normal. Such a determination can be made using the comparison 204 of the extra-cardiac response data to the extra-cardiac response information associated with equivalent levels of physiological exertion of the one or more steady state periods. Normalcy can be determined by identifying deviations in the extra-cardiac response data from that of one or more previous steady state periods, a baseline, a threshold, a pattern, or a trend, among other things. If the extra-cardiac response data is not determined 206 to be normal, then the method 200 concludes 207 that the likelihood of myocardial ischemia is relatively high, as both the cardiac response and extra-cardiac response to exertion data indicators signaled myocardial ischemia. If the extra-cardiac response data is determined 206 to be normal, then the method 200 concludes 208 that the likelihood of myocardial ischemia is relatively moderate, as only the cardiac response to exertion data indicator signaled myocardial ischemia and the extra-cardiac response to exertion data indicator did not signal myocardial ischemia.

Depending on the outcome of step 206, it may be determined 209 whether the extra-cardiac response data is normal. Such a determination can be made using the comparison 204 of the extra-cardiac response data to the extra-cardiac response information associated with equivalent levels of physiological exertion of the one or more steady state periods. If the extra-cardiac response data is not determined 209 to be normal, then the method 200 concludes 208 that the likelihood of myocardial ischemia is relatively moderate, as only the extra-cardiac response to exertion data indicator signaled myocardial ischemia while the cardiac response to exertion data indicator did not signal myocardial ischemia. If the extra-cardiac response data is determined 209 to be normal, then the method 200 concludes 210 that the likelihood of myocardial ischemia is relatively low, as both the cardiac response and extra-cardiac response to exertion data indicators did not signal myocardial ischemia.

Figure 3:
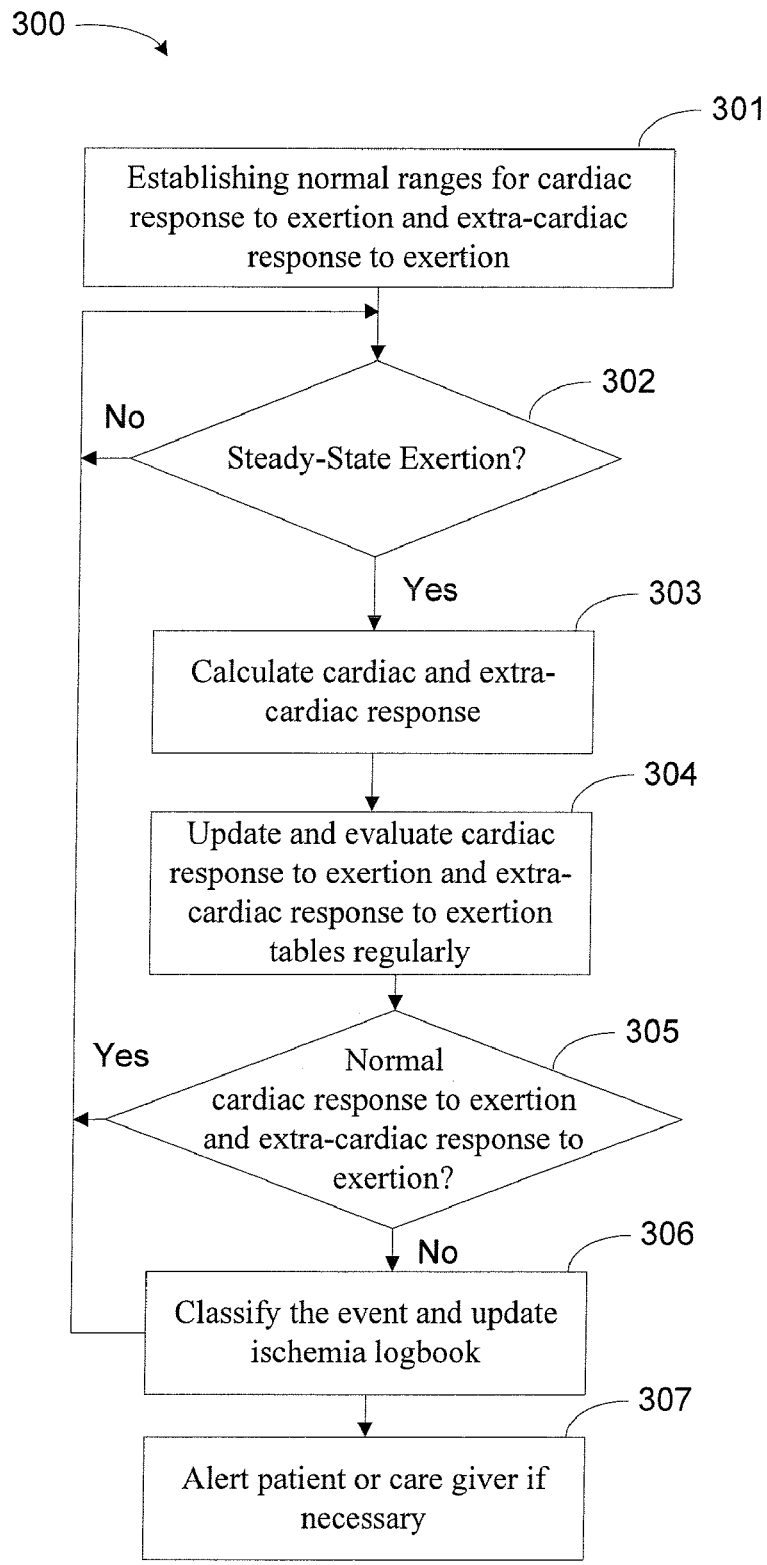
FIG. 3 is a flow diagram showing a method for characterizing a response to exertion in accordance with various embodiments of the present invention.
Figure 7:
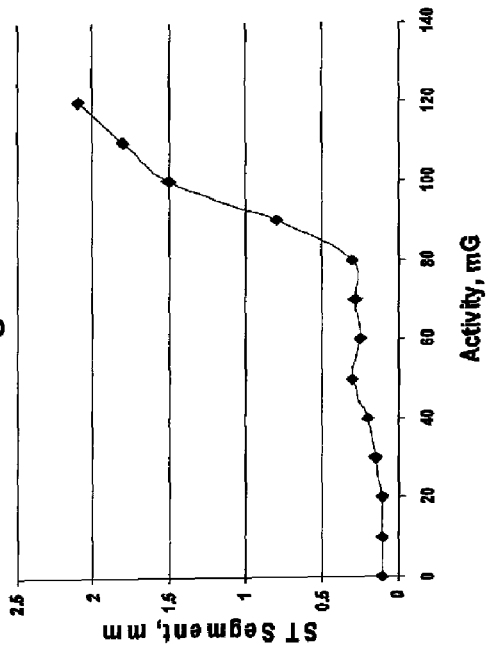
FIGS. 6-9 show plots of cardiac and extra-cardiac response data over a range of exertion levels in accordance with various embodiments of the present invention.

FIG. 3 illustrates a method 300 for detecting myocardial ischemia during exertion according to various embodiments of the invention. The method 300 includes establishing 301 normal ranges for cardiac response to exertion and extra-cardiac response to exertion. Such ranges can be establishes based on prior steady state periods of exertion for a patient, data for a general or specific population, or specified by a doctor, for example. Such ranges can be stored in memory. Multiple normal ranges could be established 301 for respective sub-ranges within the range. Such ranges can be updated regularly or upon arrival of new data.

It is then determined 302 whether steady-state exertion is sensed. The exertion could be static exertion or dynamic exertion. Furthermore, the exertion could be sensed using an implantable pressure sensor, accelerometer, implantable electromyogram (EMG) sensor, among others. The period of a sustained exertion activity can vary between embodiments and exertion parameters. For example, in one embodiment two seconds of increased intrathoracic pressure may be required to qualify as steady-state static exertion while sixty second of sustained accelerometer activity is required to qualify as steady state dynamic exertion, although not all embodiments are so limited. In another embodiment, ten seconds of increased pulmonary pressure may be required to qualify as steady-state static exertion while ten seconds of sustained lower leg EMG activity is required to qualify as steady state dynamic exertion.

If steady state exertion is not detected 302, the method 300 returns to step 302 to continue monitoring for an episode of steady state exertion. When steady state exertion is determined 302 to be occurring, or having occurred, a cardiac response and an extra-cardiac response to the steady-state exertion are calculated 303. Such calculation 303 can be based on sensed cardiac response data and extra-cardiac response data associated with the episode of steady-state exertion.

Cardiac response to exertion and the extra-cardiac response to exertion tables and plots can then be updated and evaluated 304. Examples of such tables are provided in FIGS. 4 and 5 and examples of such plots are provided in FIGS. 6-9. Using the tables and/or plots, it can be determined 305 whether the cardiac response and extra-cardiac response to the steady-state exertion were normal. In some embodiments, exhibiting a linear trend is normal, while an overall non-linear relationship between response data and exertion is abnormal and indicative of myocardial ischemia. For example, the cardiac response and extra-cardiac response to the steady-state exertion may be normal if they fit (e.g., least-squares regression trend fit) data of the tables for equivalent exertion levels. In some embodiments, the cardiac response and extra-cardiac response to the steady-state exertion may be abnormal if they fail to follow one or more trends of the tables for equivalent exertion levels. In some embodiments, the cardiac response and/or extra-cardiac response to the steady-state exertion may be abnormal if the associated data exceeds a predetermined threshold or shows erratic patterns indicative of instability.

If the cardiac response and extra-cardiac response to the steady-state exertion were determined 305 to be normal, then the method 300 returns to step 302 to monitor for further periods of steady-state exertion. If the cardiac response and extra-cardiac response to the steady-state exertion were not determined 305 to be normal, then the event is classified 306 as an ischemic event and a logbook is updated. Such event classification can be done according to the methods of event classification discussed herein. In some embodiments, a patient and/or care giver can be alerted 307 if the classified event is of a dangerous or urgent nature. In some embodiments, the method 300 returns to step 302 to monitor for further periods of steady-state exertion FIGS. 4 and 5 show tables of sample extra-cardiac response (FIG. 4) and cardiac response (FIG. 5) to exertion data. The response to exertion data of the tables is arranged according to sub-ranges of dynamic exertion (401 and 501) measured in milli-gravity (mg, as thousandths of gravitational acceleration ($3.81 \text{ m/s}^2$)) by an accelerometer. Minute ventilation 402 as sensed by impedance is determined for each sub-range level of exertion 401, among other types of extra-cardiac response data. For cardiac response data, ST segment deviation 502, feature correlation coefficient 503, occurrence of premature ventricular contractions 504, and atrial fibrillation percentage 505 are determined as organized along the sub-range levels of exertion 501.

As can be seen from the cardiac response data, atrial fibrillation percentage 504 has a rise between 30-50 mg, a decrease between 60-70 mg, and another rise between 80-120 mg. This behavior can be of particular interest to a physician as it shows trends that mere interpolation may not have shown. Subsequent samples of cardiac response data fitting this trend may be determined to be normal, whereas without this insight a spike in AF % around 30-50 mg may be incorrectly interpreted to be a premature rise of the AF % usually seen at 80-120 mg and wrongly concluded to be a change in pathology.

Figure 9:
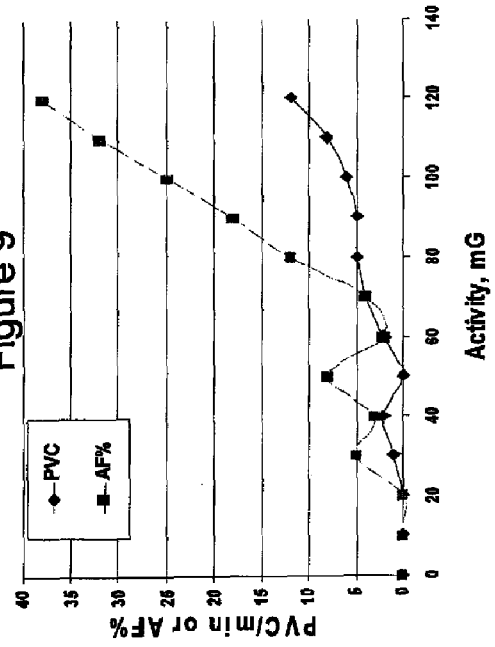
Figure 6:
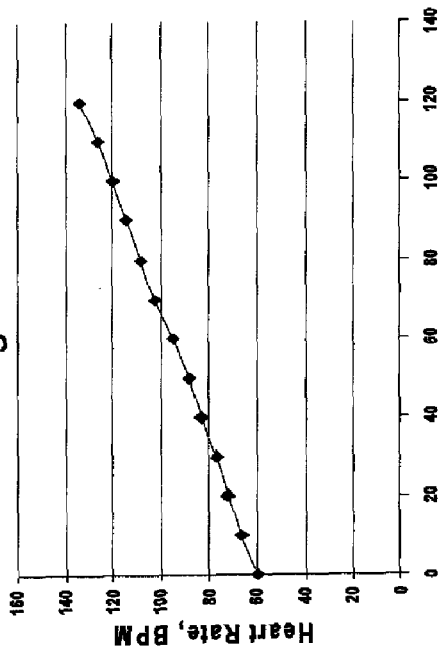
Figure 8:
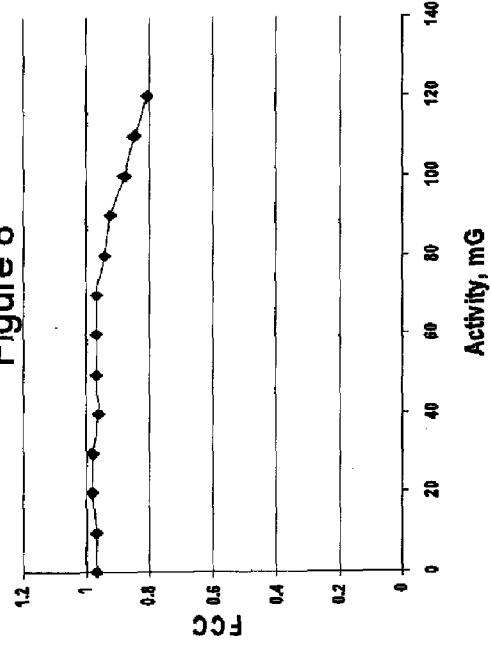

FIGS. 6-9 illustrate plots of cardiac responses to exertion. The normalcy of cardiac and extra-cardiac response to exertion can be determined from these plots. For example, FIG. 6 shows that heart rate steadily increases with increasing dynamic exertion. Such a linear relationship can indicate that the cardiac response to exertion is normal. The feature correlation coefficient data of FIG. 8 shows a nonlinear relation between activity and FCC, in which FCC drops only at higher activity levels. ST segment of FIG. 7 and atrial fibrillation percentage of FIG. 9 show a more erratic relationship to increasing dynamic exertion, but both generally rise at higher exertion levels. All of these parameters can indicate that the cardiac response to exertion is abnormal. Multiple cardiac parameters and/or multiple extra-cardiac parameters maybe compared to determine the normalcy of physiological response to exertion and detect and classify myocardial ischemia.

The plots of FIGS. 6-9 can represent previously taken response data, to which subsequent plots of response data are compared to determine normalcy, such as deviation from trends, regression analysis, and feature fit, among others.

In some embodiments, it can be useful to establish a baseline static and/or dynamic exertion/physiological response relationship to monitor cardiac function and evaluate the normalcy of steady state periods. In this way, a device may be calibrated in a clinical setting and/or periodically (e.g., daily voluntary test). Calibration can include having a patient perform the Valsalva maneuver or bowel movement, for example, to determine a response to static exertion. Calibration can be performed by having the patient perform the Valsalva maneuver at load pressures of 10, 20, and 30 mmHg, cardiac and extra-cardiac response signals being measured during each test. Likewise, a patient may undergo a fitness test (e.g., walking) at various levels of intensity to determine standard cardiac and extra-cardiac response to exertion across the levels of exertion intensity. The generated sensor signals can then be tabulated for use as a calibration standard (e.g., baseline) to assess later deviations, which can be indicative of abnormal cardiac functions and myocardial ischemia.

The tables, plots, and methods illustrated and/or described herein can be used to classify myocardial ischemia, predict occurrences of myocardial ischemia and provide a warning and/or provide a therapy. Prior periods of myocardial ischemia can be used to establish an exertional threshold (e.g., as measured by intrathoracic pressure and/or accelerometer activity), above which physiological complications associated with myocardial ischemia are likely. Multiple thresholds can be established for different types of physiological complications (e.g., one exertional threshold for dyspnea and another for palpitations).

For example, a pattern maybe recognized based on past steady state periods where if a patient's static exertion intensity (e.g., pleural cavity pressure) reaches a certain level, then the patient is likely to experience a PVC, or other cardiac complication. If a device senses that the patient's static exertion exceeds that threshold, and abnormal cardiac and/or extra-cardiac responses are observed, then the device may facilitate alerting the patient and/or health professional of the condition such that behavioral and environmental stressors can be addressed. In some embodiments, a device such as a pacer and/or drug delivery device may take appropriate action (e.g., deliver an electrical cardiac therapy tailored to account for the particular cardiac condition associated with the exertion level or deliver a pharmaceutical that addresses myocardial ischemia).

Such embodiments are particularly advantageous in view of static exertion, as a patient may not generally associate a non-ambulatory position with behavior that can stress the cardiovascular system and lead to myocardial ischemia. As such, aspects of the invention can help a patient be more aware of, and avoid, behavioral and environmental stressors that would not otherwise be associated with myocardial ischemia. Furthermore, implantable devices can be more sensitive to myocardial ischemia and anticipate and address physiological problems associated with exertion and myocardial ischemia.

FIGS. 10-14 illustrate various plots of cardiac response to exertion and extra-cardiac response to exertion. These figures demonstrate, among other things, how normalcy, patterns, deviations, fit, and the like can be determined. For example, FIG. 10 shows a pattern of cardiac response to exertion data whereby the cardiac response follows a step function (a distinct increase at a certain level of activity). The cardiac response level is fairly constant at two different levels of cardiac response, one of the levels being shown by trend line 1001. In one embodiment, if the data were to indicate ST segment, a normal response would be expected to have a flat pattern (e.g., consistent level). However, the bi-level pattern of FIG. 10 indicates abnormal ST segment response, for example.

FIGS. 10-14 can further be used to characterize myocardial ischemia as exertion or non-exertion related ischemia. Moreover, when combined with evidence of chest pain (e.g., patient reported) then such methods can characterize angina as stable, unstable, and vasospasm. Based on cardiac response data, a threshold 1002 of activity can be established at the step transition between the two levels of cardiac response. If a subsequent set of cardiac response to exertion data does not fit one or more of the patterns of FIG. 10, such as if the cardiac response data does not plane out at the response levels (e.g., 1401) or does not transition between levels at the same threshold 1402, then the data may be determined to be indicative of non-exertion related myocardial ischemia and if present with chest pain, unstable angina. FIG. 12 is an example of erratic data that does not fit the trends of FIG. 10 and is indicative of non-exertion related ischemia (and unstable angina) because the data does not show a proportional relationship between the physiological response and exertion intensity.

In some embodiments, presence of a proportional relationship between physiological response (e.g., shown by cardiac and/or extra-cardiac response data) and exertion intensity can show whether myocardial ischemia is exertion related or non-exertion related. For example, if increasing exertion shows a proportional change in a physiological parameter indicative of myocardial ischemia, then the myocardial ischemia can be classified as exertion-related. However, if the physiological parameter shows no relationship to exertion intensity (e.g., the data is erratic data) then the myocardial ischemia is non-exertion related.

FIG. 11 shows a pattern of extra-cardiac response to exertion, whereby two slopes trends 1101 and 1102, and a threshold 1103 between them, can be identified. The data presented in FIG. 11 can be determined to be abnormal because of the two different slopes 110 and 1102 (as opposed to a more consistent correlation between extra-cardiac response and exertion level). Subsequent data that does not fit these trends, such as having two slopes or having different slope values, can be determined to be unstable angina. FIG. 13 shows an erratic extra-cardiac response to exertion data that does not fit the trends of FIG. 11, and can be determined to indicate unstable angina on that basis.

Transition thresholds 1002 and 1103 can also correspond to angina thresholds, whereby angina is experienced at levels of exertion beyond the thresholds 1002 and 1103 (where the trends exhibited below the thresholds are broken). As such, these thresholds 1002 and 1103 and methods described herein can be used to predict and classify episodes of angina. Patient feedback can be used to confirm that chest pain or other symptom(s) was experienced corresponding to breach of an angina threshold. An angina threshold can be established based on prior episodes, a patient and/or doctor warned during subsequent episodes of exertion when the level of exertion intensity approaches and/or breaches an angina threshold. In such cases, therapeutic action, such as automatic drug delivery or a cardiac electrical therapy delivery, can be initiated or modified based on a current level of exertion approaching or exceeding the angina threshold.

Based on consistent or erratic patterns of extra-cardiac response and/or cardiac response, an ischemia episode can further be classified into stable angina, unstable angina, or vasospasm. If extra-cardiac response and cardiac response demonstrates a two-piecewise linear relationship with a clean turning point, the episode is likely to be a stable angina, with the exertion level at the turning point being the exertion threshold for angina. If the extra-cardiac response or cardiac response demonstrates an erratic pattern with frequent occurrence of abnormal values in a short period of time (e.g., a couple of minutes) the episode is likely to be an unstable angina. If the abnormal response is observed during static exertion, the episode is likely to be a vasospasm.

FIGS. 10 and 11 are examples of stable angina, where the response data fits trends 1001, 1002, 1101, and 1102. FIGS. 12 and 13 are examples of unstable angina, where the response data does not fit trends 1001, 1002, 1101, and 1102 and is generally erratic. In some embodiments, episodes of stable angina can be distinguished from unstable angina not from a comparison to trends, but on having scattered data with a number of outlying response measurements. For example, angina may be said to be unstable if cardiac response data to exertion has three or more outlying measurements of cardiac response to exertion, as shown in FIG. 12.

The cardiac and extra-cardiac responses to static exertion can be assessed by developing the following parameters based on the exertion (static and dynamic) and response measurements (cardiac and extra-cardiac): maximal values, slopes of signals (e.g., slopes to maximum signal values and slopes to physiological recovery, 1101), gain (maximum exertion/maximum extra-cardiac response), recovery overshoot, and phase of cardiac and/or extra-cardiac response with respect to exertion (e.g., delay), among others.

The tables and plots discussed above can be used to recognize patterns useful for diagnosis and therapy initiation and/or adjustment. For example, an abnormally high heart rate and/or breathing level for given exertion level could suggest ischemia and could further trigger a therapy or alarm. A decrease in tidal volume might indicate onset of shallow breathing, which can be an indicator of ischemia). Venous oxygen saturation, as an extra-cardiac parameter, might indicate ischemia when relatively low venous oxygen saturation is detected at low exertion levels, for example. A reduction in stroke volume at a given exertion level may indicate ischemia.

Figure 15:
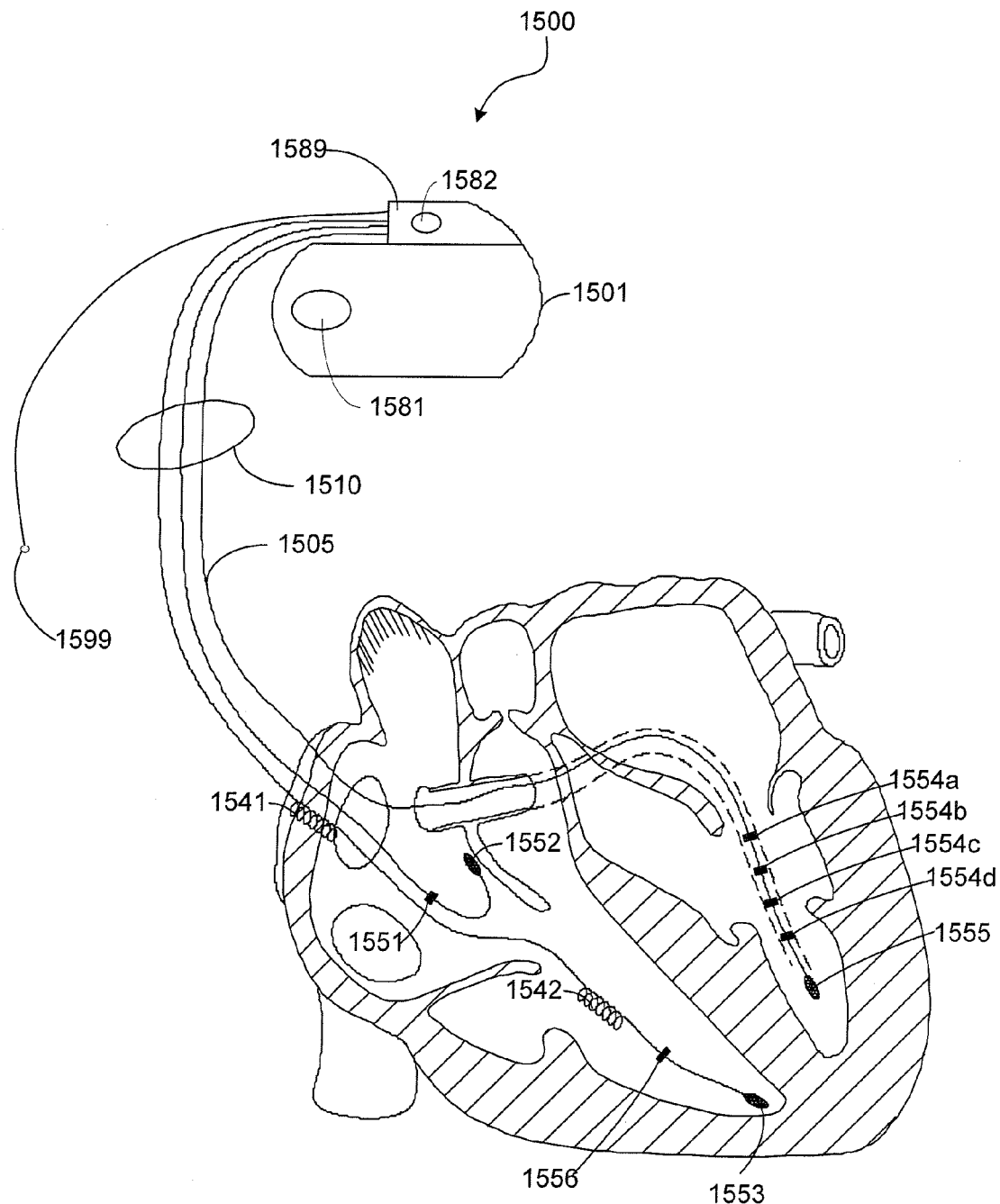
FIG. 15 illustrates a patient-implantable device that may be used in accordance with various embodiments of the present invention.

The implantable device 1500 illustrated in FIG. 15 employs circuitry capable of implementing the ischemia detection techniques described herein. The implantable device 1500 includes cardiac rhythm management (CRM) circuitry enclosed within an implantable housing 1501. The CRM circuitry is electrically coupled to an intracardiac lead system 1510. Although an intracardiac lead system 1510 is illustrated in FIG. 15, various other types of lead/electrode systems may additionally or alternatively be deployed. For example, the lead/electrode system may comprise an epicardial lead/electrode system including electrodes outside the heart and/or cardiac vasculature, such as a heart sock, an epicardial patch, and/or a subcutaneous system having electrodes implanted below the skin surface but outside the ribcage.

Portions of the intracardiac lead system 1510 are inserted into the patient's heart. The lead system 1510 includes cardiac pace/sense electrodes 1551-1556 positioned in, on, or about one or more heart chambers for sensing electrical signals from the patient's heart and/or delivering pacing pulses to the heart. The intracardiac sense/pace electrodes 1551-1556, such as those illustrated in FIG. 15, may be used to sense and/or pace one or more chambers of the heart, including the left ventricle, the right ventricle, the left atrium and/or the right atrium. The CRM circuitry controls the delivery of electrical stimulation pulses delivered via the electrodes 1551-1556. The electrical stimulation pulses may be used to ensure that the heart beats at a hemodynamically sufficient rate, may be used to improve the synchrony of the heart beats, may be used to increase the strength of the heart beats, and/or may be used for other therapeutic purposes to support cardiac function consistent with a prescribed therapy.

The lead system 1510 includes defibrillation electrodes 1541, 1542 for delivering defibrillation/cardioversion pulses to the heart.

The left ventricular lead 1505 incorporates multiple electrodes 1554a-1554d and 1555 positioned at various locations within the coronary venous system proximate the left ventricle. Stimulating the ventricle at multiple locations in the left ventricle or at a single selected location may provide for increased cardiac output in a patients suffering from congestive heart failure (CHF), for example, and/or may provide for other benefits. Electrical stimulation pulses may be delivered via the selected electrodes according to a timing sequence and output configuration that enhances cardiac function. Although FIG. 15 illustrates multiple left ventricle electrodes, in other configurations, multiple electrodes may alternatively or additionally be provided in one or more of the right atrium, left atrium, and right ventricle.

The implantable device 1500 can include a pressure sensor 1599 configured to be positioned within the pleural space to measure static pressure. One or more pressure sensors can additionally or alternatively be positioned on the lead system 1510 and housing 1501.

Portions of the housing 1501 of the implantable device 1500 may optionally serve as one or more multiple can 1581 or indifferent 1582 electrodes. The housing 1501 is illustrated as incorporating a header 1589 that may be configured to facilitate removable attachment between one or more leads and the housing 1501. The housing 1501 of the implantable device 1500 may include one or more can electrodes 1581. The header 1589 of the implantable device 1500 may include one or more indifferent electrodes 1582. The can 1581 and/or indifferent 1582 electrodes may be used to deliver pacing and/or defibrillation stimulation to the heart and/or for sensing electrical cardiac signals of the heart.

Communications circuitry is disposed within the housing 1501 for facilitating communication between the CRM circuitry and a patient-external device, such as an external programmer or advanced patient management (APM) system. The implantable device 1500 may also include sensors and appropriate circuitry for sensing a patient's metabolic need and adjusting the pacing pulses delivered to the heart and/or updating the electrode combination selection to accommodate the patient's metabolic need.

In some implementations, an APM system may be used to perform some of the processes discussed here, including evaluating, estimating, comparing, selecting, and updating, among others. Methods, structures, and/or techniques described herein, may incorporate other various structure, features, and methodologies, including those described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference in each of their respective entireties.

In certain embodiments, the implantable device 1500 may include circuitry for detecting and treating cardiac tachyarrhythmia via defibrillation therapy and/or anti-tachyarrhythmia pacing (ATP). Configurations providing defibrillation capability may make use of defibrillation coils 1541, 1542 for delivering high energy pulses to the heart to terminate or mitigate tachyarrhythmia.

CRM devices using multiple electrodes, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-electrode pacemaker has the capability of switching the output of pacing pulses between selected electrode combinations within a heart chamber during different cardiac cycles.

The implantable device 1500 may incorporate a motion detector that may be used to sense various respiration-related conditions. For example, a motion detector may be configured to activity level and/or chest wall movements, which can be associated with respiratory effort, for example. The motion detector may be implemented as an accelerometer positioned in or on the housing 1501 of the implantable device 1500.

The lead system 1510 of the implantable device 1500 may incorporate one or more transthoracic impedance sensors that may be used to acquire the patient's respiration waveform, or other respiration-related information. The transthoracic impedance sensor may include, for example, one or more intracardiac electrodes 1541, 1542, 1551-1556 positioned in one or more chambers of the heart. The intracardiac electrodes 1541, 1542, 1551-1556 may be coupled to impedance drive/sense circuitry positioned within the housing of the implantable device 1500.

In one implementation, impedance drive/sense circuitry generates a current that flows through the tissue between an impedance drive electrode 1551 and a can electrode on the housing 1501. The voltage at an impedance sense electrode 1552 relative to the can electrode changes as the patient's transthoracic impedance changes. The voltage signal developed between the impedance sense electrode 1552 and the can electrode is detected by the impedance sense circuitry. Other locations and/or combinations of impedance sense and drive electrodes are also possible.

The voltage signal developed at the impedance sense electrode 1552 is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions.

Figure 16:
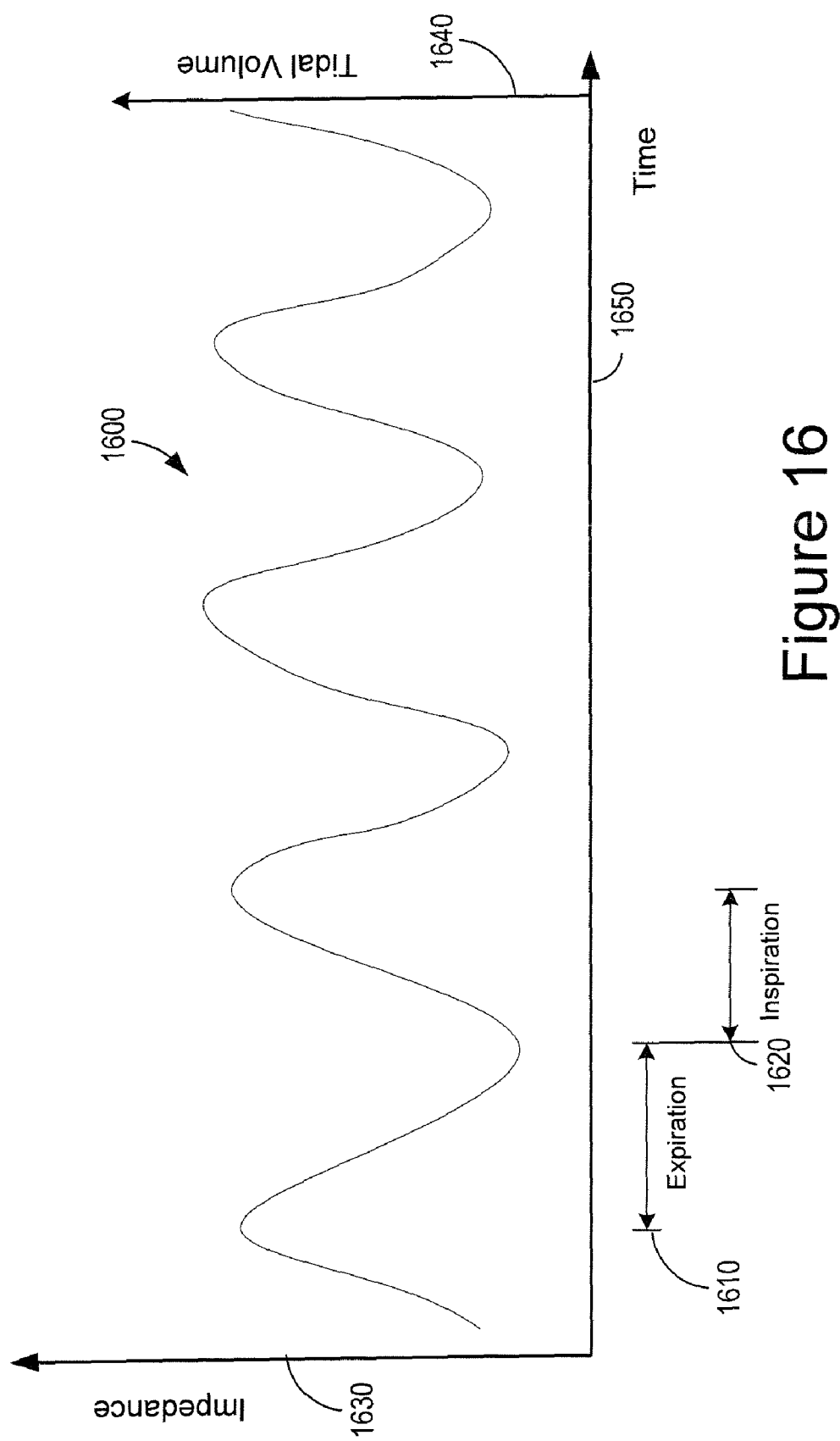
FIG. 16 illustrates an impedance plot that may be used to characterize respiration in accordance with various embodiments of the present invention.

FIG. 16 illustrates an impedance based respiration signal that may be taken using, for example, the electrodes of the implantable device 1500 of FIG. 15.

FIG. 16 illustrates an impedance signal 1600. The impedance signal 1600 may be developed, for example, from an impedance sense electrode in combination with an implantable device, as discussed herein. The impedance signal 1600 is proportional to the transthoracic impedance, illustrated as impedance 1630 on the abscissa of the left side of the graph in FIG. 16.

The impedance 1630 increases during any respiratory inspiration 1620 and decreases during any respiratory expiration 1610. The impedance signal 1600 is also proportional to the amount of air inhaled, denoted by a tidal volume 1640, illustrated on the abscissa of the right side of the graph in FIG. 16. The variations in impedance during respiration, identifiable as the peak-to-peak variation of the impedance signal 1600, may be used to determine the respiration tidal volume 1640. Tidal volume 1640 corresponds to the volume of air moved in a breath, one cycle of expiration 1610 and inspiration 1620. A minute-ventilation may also be determined, corresponding to the amount of air moved per a minute of time 1650 illustrated on the ordinate of the graph in FIG. 16.

Figure 17:
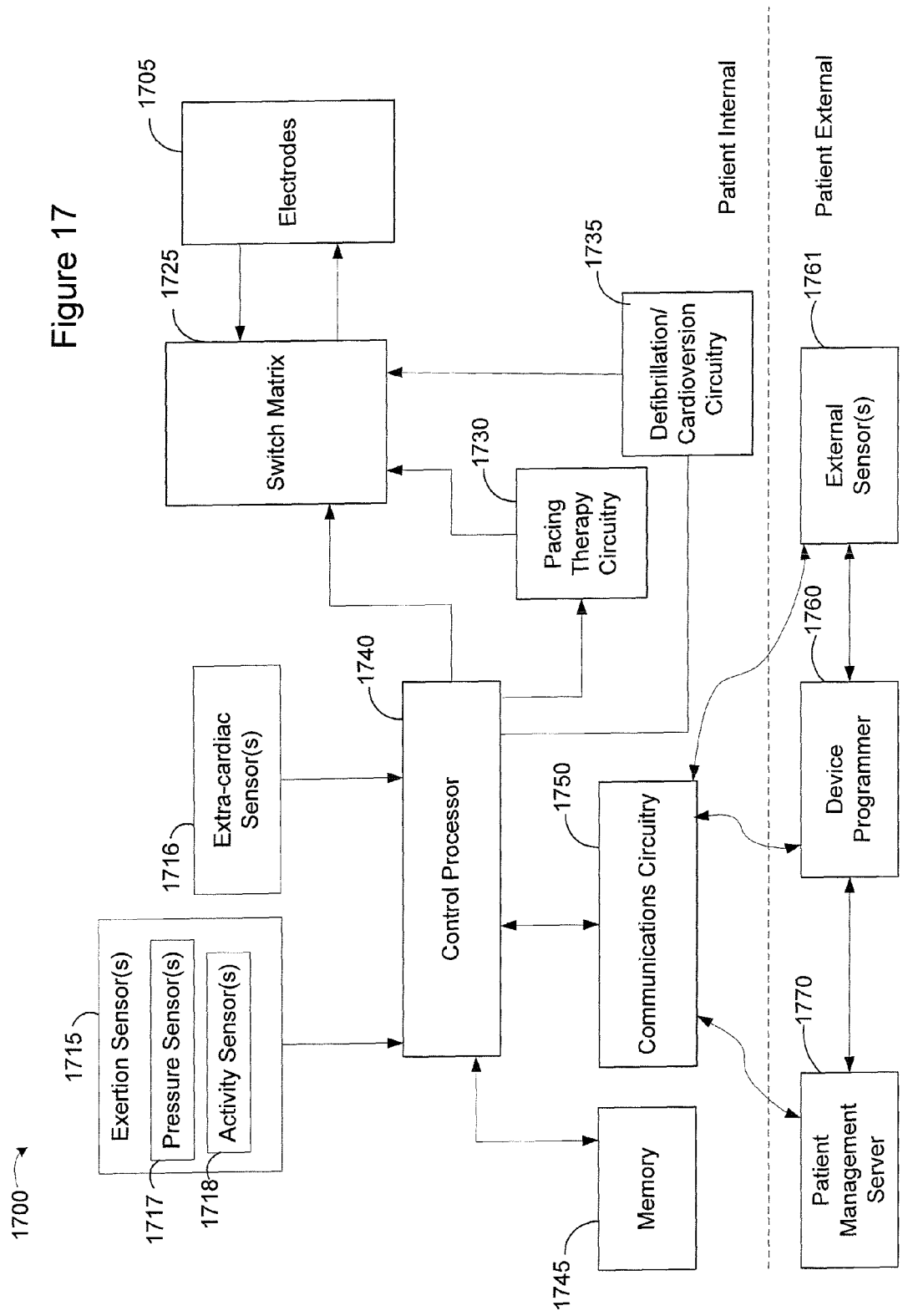
FIG. 17 shows block circuitry diagrams of a patient implantable medical device and external devices in accordance with various embodiments of the present invention.

FIG. 17 is a block diagram of an implantable device 1700 that may incorporate circuitry for detecting myocardial ischemia in accordance with embodiments of the present invention. The implantable device 1700 may include pacing therapy circuitry 1730 that delivers pacing pulses to a heart. The implantable device 1700 may optionally include defibrillation/cardioversion circuitry 1735 configured to deliver high energy defibrillation or cardioversion stimulation to the heart for terminating dangerous tachyarrhythmias.

The pacing pulses are delivered to the heart via multiple electrodes 1705 (electrode combinations) disposed at multiple locations within a heart and/or in subcutaneous non-intrathoracic locations. One or more electrodes may be disposed within a single heart chamber. The electrodes 1705 are coupled to switch matrix 1725 circuitry used to selectively couple electrodes 1705 of various pacing configurations to electrode control processor 1740 and/or other components of the implantable device 1700.

The control processor 1740 can use information received from electrodes 1705, exertion sensors 1715, and extra-cardiac sensors 1716 to detect and classify myocardial ischemia, among other functions.

Exertion sensors 1715 can comprise one or more pressure sensors 1717 and activity sensors 1718. The pressure sensors 1717 can comprise piezoelectric elements, among other pressure sensing means.

Activity sensors 1718 can include an inclination sensor, posture monitor, and/or accelerometer, among other sensing means.

Various extra-cardiac parameters can be monitored using the extra-cardiac sensors 1716 and/or electrodes 1705. For example, impedance can be sensed using electrodes 1705, the impedance being used to determine respiration rate, tidal volume, and/or minute ventilation, among other parameters. Extra-cardiac sensors 1716 can include pH sensors, oxygen saturation sensors, acoustic sensors, electrical signal sensors, pressure sensors, strain gauges, force transducers, electrodes measuring electromyogram, and the like.

An implantable device 1700 typically includes a battery power supply (not shown) and communications circuitry 1750 for communicating with an external device programmer 1760 or other patient-external device, such as external sensor 1761. Information, such as data, parameter measurements, parameter evaluations, parameter estimates, and/or program instructions, and the like, can be transferred between the device programmer 1760, external sensors 1761, patient management server 1770, implantable device 1700 and/or other external system. In some embodiments, the control processor 1740 may be a component of the device programmer 1760, patient management server 1770, or other patient external system.

The CRM device 1700 also includes a memory 1745 for storing program instructions and/or data, accessed by and through the control processor 1740. In various configurations, the memory 1745 may be used to store information related to activation thresholds, parameters, orders, measured values, program instructions, and the like, to facilitate execution of the various methods and functions described herein by the implantable device 1700.

Some embodiments of the invention may contain a speaker or other noise producing device to provide an alert to the patient. Some embodiments of the invention may include a vibrating component to provide an alert. Alerts may also be provided by external devices (e.g., noise, vibration, display) in direct or indirect communication with an implantable medical device 1700 using communications circuitry 1750. Alerts may be provided to a patient under the various conditions discussed herein (e.g., an episode of myocardial ischemia is determined to be likely to occur or to have occurred).

Figure 18:
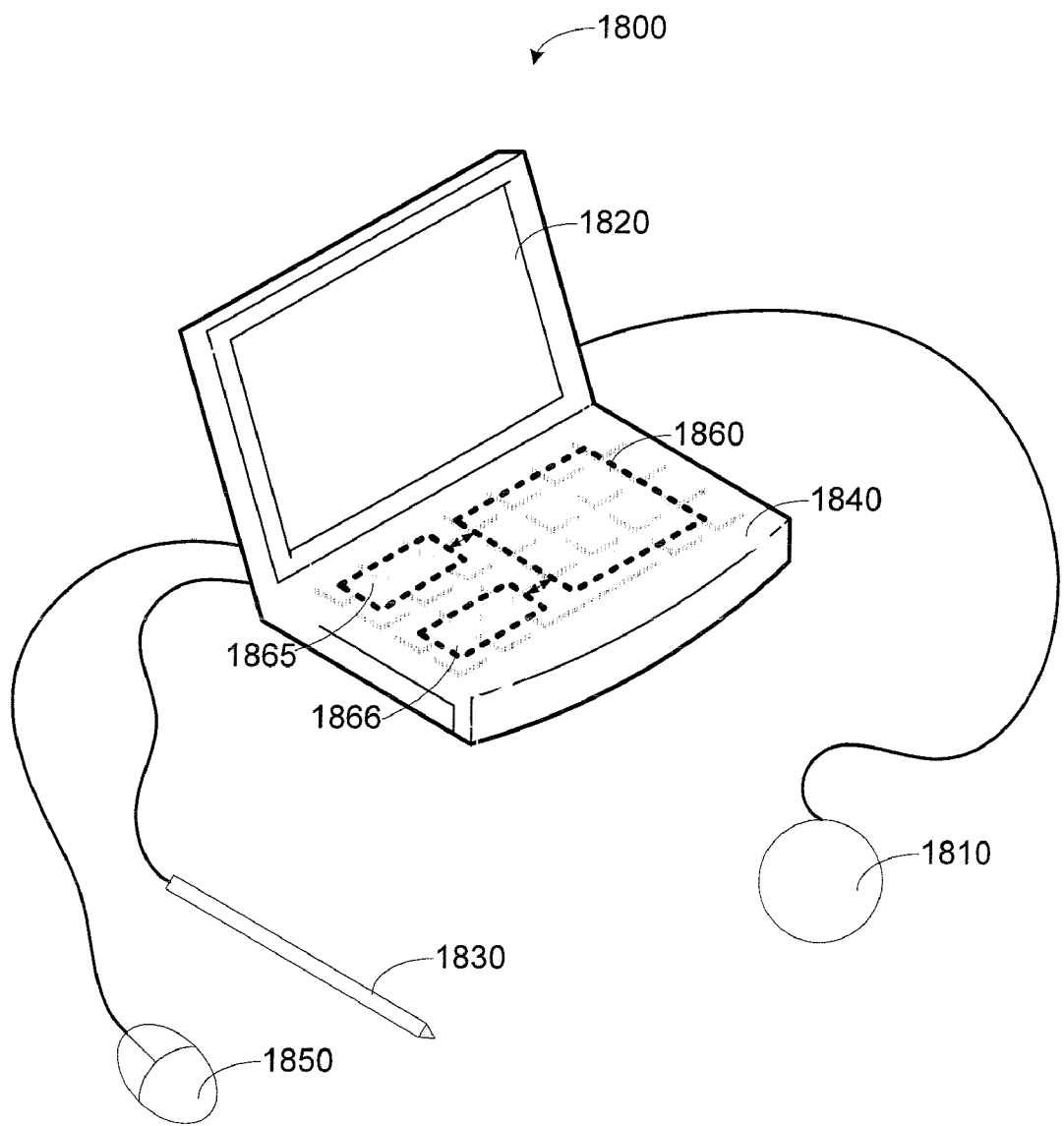
FIG. 18 illustrates a programmer device for interfacing with a patient-implantable device that may be used in accordance with various embodiments of the present invention.

FIG. 18 illustrates a patient external device 1800 that provides a user interface configured to allow a human analyst, such as a physician, or patient, to interact with an implanted medical device. The patient external device 1800 is described as a CRM programmer, although the methods of the invention are operable on other types of devices as well, such as portable telephonic devices, computers or patient information servers used in conjunction with a remote system, for example. The programmer 1800 includes a programming head 1810 which is placed over a patient's body near the implant site of an implanted device to establish a telemetry link between a CRM and the programmer 1800. The telemetry link allows the data collected by the implantable device to be downloaded to the programmer 1800. The downloaded data is stored in the programmer memory 1865.

The programmer 1800 includes a graphics display screen 1820, e.g., liquid crystal diode display screen, that is capable of displaying graphics, plots, tables, alphanumeric symbols, and/or other information. For example, the programmer 1800 may graphically display one or more of the tables of FIGS. 4-5 and/or plots of FIGS. 6-14 downloaded from the CRM on the screen 1820. The display screen 1820 may include touch-sensitive capability so that the user can input information or commands by touching the display screen 1820 with a stylus 1830 or the user's finger. Alternatively, or additionally, the user may input information or commands via a keyboard 1840 or mouse 1850.

The programmer 1800 includes a data processor 1860 including software and/or hardware for performing the methods disclosed here, using program instructions stored in the memory 1865 of the programmer 1800. In one implementation, sensed data is received from a CRM via communications circuitry 1866 of the programmer 1800 and stored in memory 1865. The data processor 1860 evaluates the sensed data, which can include data related to static exertion, dynamic exertion, cardiac activity, and/or extra-cardiac activity.

Figure 19:
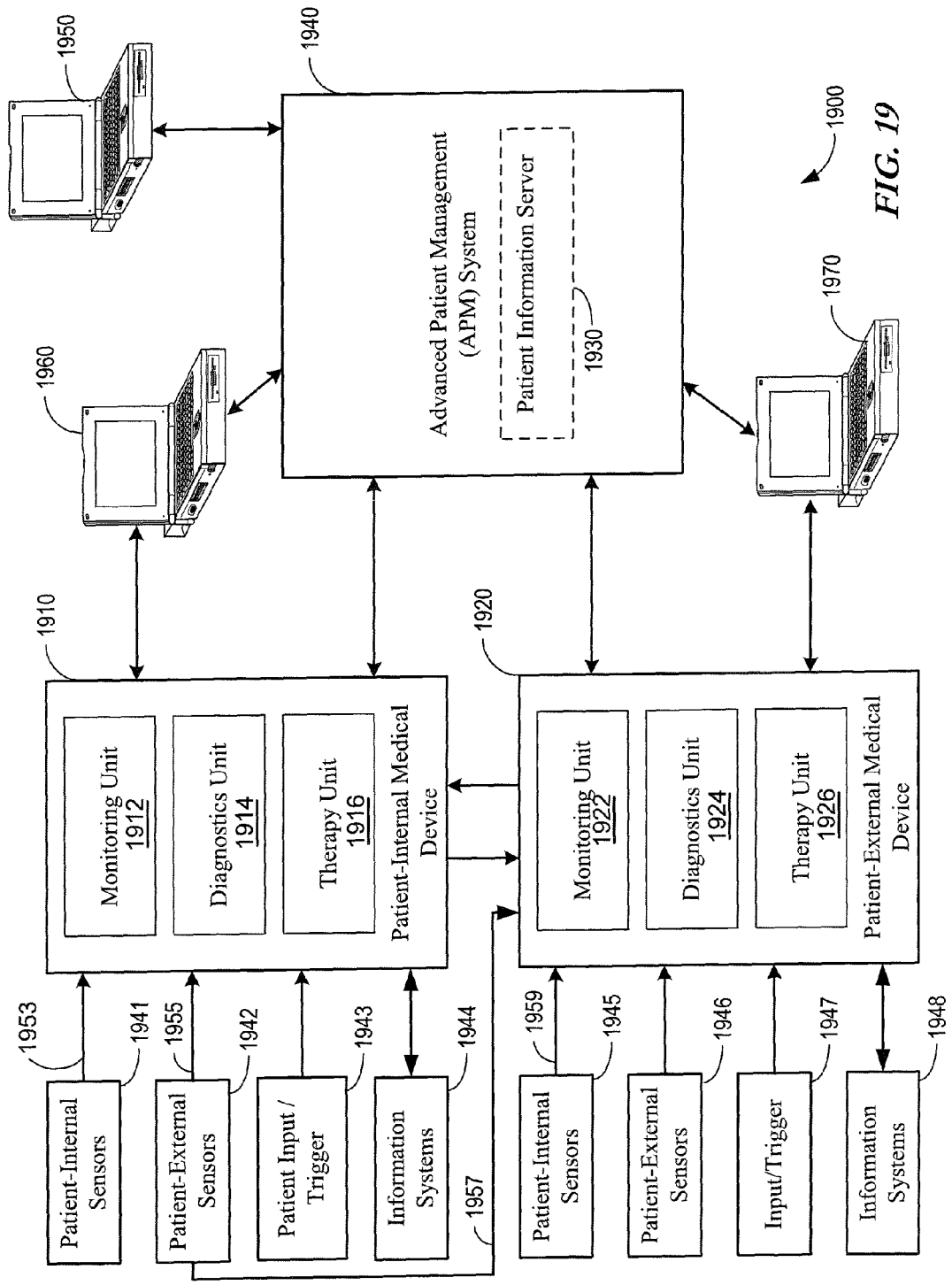
FIG. 19 illustrates an advanced patient management system that may be used in accordance with various embodiments of the present invention.

Referring now to FIG. 19, a patient implantable medical device (PIMD) of the present invention may be used within the structure of an APM system 1900. The APM system 1900 allows physicians and/or other clinicians to remotely and automatically monitor physiological functions, as well as other patient conditions. In one example, a PIMD implemented as a cardiac pacemaker, defibrillator, resynchronization device, drug pump, or neuro-stimulator may be equipped with various telecommunications and information technologies that enable real-time data collection, analysis, diagnosis, and treatment of the patient.

Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 19, the APM system 1900 may be used to implement parameter monitoring, diagnosis, exertion assessment, patient therapy, therapy selection, and/or therapy control in accordance with embodiments of the invention. The medical system 1900 may include, for example, one or more patient-internal medical devices 1910, such as a PIMD, and one or more patient-external medical devices 1920, such as a monitor or signal display device. Each of the patient-internal 1910 and patient-external 1920 medical devices may include one or more of a patient monitoring unit 1912, 1922, a diagnostics unit 1914, 1924, and/or a therapy unit 1916, 1926.

The patient-external medical device 1920 performs monitoring, and/or diagnosis and/or therapy functions external to the patient (i.e., not invasively implanted within the patient's body). The patient-external medical device 1920 may be positioned on the patient, near the patient, or in any location external to the patient to measure various parameters discussed herein externally.

The patient-internal and patient-external medical devices 1910, 1920 may be coupled to one or more sensors 1941, 1942, 1945, 1946, patient input/trigger devices 1943, 1947 and/or other information acquisition devices 1944, 1948. The sensors 1941, 1942, 1945, 1946, patient input/trigger devices 1943, 1947, and/or other information acquisition devices 1944, 1948 may be employed to detect conditions relevant to the monitoring, diagnostic, and/or therapeutic functions of the patient-internal and patient-external medical devices 1910, 1920. For example, the patient input/trigger devices 1943, 1947, and/or other information acquisition devices 1944, 1948 may be employed by a patient to input information regarding conditions experienced by the patient that could be relevant to a myocardial ischemia diagnosis, such as nausea, light-headedness, chest pain, and fatigue.

The medical devices 1910, 1920 may each be coupled to one or more patient-internal sensors 1941, 1945 that are fully or partially implantable within the patient. The medical devices 1910, 1920 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1941 may be coupled to the patient-internal medical device 1910 through one or more internal leads 1953. Still referring to FIG. 19, one or more patient-internal sensors 1941 may be equipped with transceiver circuitry to support wireless communications between the one or more patient-internal sensors 1941 and the patient-internal medical device 1910 and/or the patient-external medical device 1920. The patient-internal sensors 1945 may be coupled to the patient-external medical device 1920 through a wireless connection 1959, and/or using communications between the patient-internal medical device 1910 and the patient-external medical device 1920, or may be coupled using a wire or other communications channel.

The patient-external sensors 1942 may be coupled to the patient-internal medical device 1910 through one or more internal leads 1955. Patient-external sensors 1942 may communicate with the patient-internal medical device 1910 wirelessly. Patient-external sensors 1942 may be coupled to the patient-external medical device 1920 through one or more leads 1957 or through a wireless link.

In various embodiments, the patient-external medical device 1920 includes a visual display configured to concurrently display extra-cardiac signals and cardiac signals and/or display one or more of the tables of FIGS. 4-5 and/or plots of FIGS. 6-14.

Referring still to FIG. 19, the medical devices 1910, 1920 may be connected to one or more information acquisition devices 1944, 1948, such as a database that stores information useful in connection with the monitoring, diagnostic, or therapy functions of the medical devices 1910, 1920. For example, one or more of the medical devices 1910, 1920 may be coupled through a network to a patient information server 1930.

The input/trigger devices 1943, 1947 are used to allow the physician, clinician, and/or patient to manually trigger and/or transfer information to the medical devices 1910, 1920 and/or from the APM system 1940 and/or patient-external medical device 1920 back to the patient-internal device 1910. The input/trigger devices 1943, 1947 may be particularly useful for inputting information concerning patient perceptions, such as a perceived cardiac event, fatigue, chest pain, how well the patient feels, and other information not automatically sensed or detected by the medical devices 1910, 1920. For example, the patient may trigger the input/trigger device 1943 upon perceiving a cardiac event. The trigger may then initiate the recording of cardiac signals and/or other sensor signals in the patient-internal device 1910. Later, a clinician may trigger the input/trigger device 1947, initiating the transfer of the recorded cardiac and/or other signals from the patient-internal device 1910 to the patient-external device 1920 for display and diagnosis.

In one embodiment, the patient-internal medical device 1910 and the patient-external medical device 1920 may communicate through a wireless link between the medical devices 1910, 1920. For example, the patient-internal and patient-external devices 1910, 1920 may be coupled through a short-range radio link, such as Bluetooth, IEEE 802.11 and/or a proprietary wireless protocol. The communications link may facilitate uni-directional or bi-directional communication between the patient-internal 1910 and patient-external 1920 medical devices. Data and/or control signals may be transmitted between the patient-internal 1910 and patient-external 1920 medical devices to coordinate the functions of the medical devices 1910, 1920.

In another embodiment, patient data may be downloaded from one or more of the medical devices periodically or on command, and stored at the patient information server 1930. The physician and/or the patient may communicate with the medical devices and the patient information server 1930, for example, to acquire patient data or to initiate, terminate, or modify recording and/or therapy.

The data stored on the patient information server 1930 may be accessible by the patient and the patient's physician through one or more terminals 1950, e.g., remote computers located in the patient's home or the physician's office. The patient information server 1930 may be used to communicate to one or more of the patient-internal and patient-external medical devices 1910, 1920 to provide remote control of the monitoring, diagnosis, and/or therapy functions of the medical devices 1910, 1920.

In one embodiment, the patient's physician may access patient data transmitted from the medical devices 1910, 1920 to the patient information server 1930. After evaluation of the patient data, the patient's physician may communicate with one or more of the patient-internal or patient-external devices 1910, 1920 through an APM system 1940 to initiate, terminate, or modify the monitoring, diagnostic, and/or therapy functions of the patient-internal and/or patient-external medical systems 1910, 1920.

In another embodiment, the patient-internal and patient-external medical devices 1910, 1920 may not communicate directly, but may communicate indirectly through the APM system 1940. In this embodiment, the APM system 1940 may operate as an intermediary between two or more of the medical devices 1910, 1920. For example, data and/or control information may be transferred from one of the medical devices 1910, 1920 to the APM system 1940. The APM system 1940 may transfer the data and/or control information to another of the medical devices 1910, 1920.

In one embodiment, the APM system 1940 may communicate directly with the patient-internal and/or patient-external medical devices 1910, 1920. In another embodiment, the APM system 1940 may communicate with the patient-internal and/or patient-external medical devices 1910, 1920 through medical device programmers 1960, 1970 respectively associated with each medical device 1910, 1920. As was previously stated, the patient-internal medical device 1910 may take the form of an implantable PIMD.

Various embodiments of the invention can use all or selected aspects/features described or illustrated in the preceding figures. For example, the implantable device of FIG. 15 may contain the circuitry of FIG. 17, interface with the programmer of FIG. 18, and serve as the patient internal medical device of FIG. 19 to carry out each of the methods discussed herein (e.g., FIGS. 1-3) and generate the tables and plots of FIGS. 4-14.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system for characterizing myocardial ischemia, comprising:
    an implantable static exertion sensor configured to output an exertion signal responsive to patient static exertion, the exertion signal containing static exertion data;
    at least one implantable physiological parameter sensor configured to output a physiological signal responsive to a physiological parameter, the physiological signal containing physiological exertion-response data, the at least one implantable physiological parameter sensor comprising:
        an implantable extra-cardiac parameter sensor configured to output an extra-cardiac signal responsive to an extra-cardiac parameter, the extra-cardiac signal containing extra-cardiac response data; and
        an implantable cardiac parameter sensor configured to output a cardiac signal responsive to a cardiac parameter, the cardiac signal containing cardiac response data;
    memory; and
    a processor configured to execute program instructions stored in memory to cause the system to:
        identify steady state periods of physiological exertion based on the static exertion data and assign one of a plurality of exertion intensity levels to each of the steady state periods;
        organize the physiological exertion-response data according to the assigned exertion intensity levels of the identified steady state periods of physiological exertion during which the physiological exertion-response data was respectively output;
        compare the physiological exertion-response data with stored physiological response information associated with equivalent levels of physiological exertion intensity of the steady state periods to which the physiological exertion-response data is organized; and
        determine the likelihood that myocardial ischemia occurred during one or more of the periods based on the comparison of the physiological response information to the physiological exertion-response data, wherein:
            processor organization of the physiological response data comprises organizing the respective extra-cardiac response and cardiac response data according to the assigned exertion intensity levels of the identified steady state periods of physiological exertion during which the extra-cardiac response and cardiac response data was respectively output;
            processor comparison of the physiological exertion-response data with stored physiological response information comprises respectively comparing the extra-cardiac and cardiac response data with extra-cardiac and cardiac response information associated with equivalent levels of physiological exertion intensity of the steady state periods to which the extra-cardiac and cardiac response data is organized; and
            determining the likelihood that myocardial ischemia occurred during one or more of the periods is based on the comparison of the extra-cardiac and cardiac response data to the extra-cardiac and cardiac response information.

2. The system of claim 1, wherein:
    the likelihood that myocardial ischemia occurred during a period of the identified steady state periods is determined to be relatively high if both the extra-cardiac response data and the cardiac response data for the period deviate from trends of the extra-cardiac response information and the cardiac response information;
    the likelihood that myocardial ischemia occurred during the period is determined to be relatively moderate if only one of the extra-cardiac response data and the cardiac response data for the period deviate from trends of the extra-cardiac response information and the cardiac response information; and
    the likelihood that myocardial ischemia occurred during the period is determined to be relatively low if neither of the extra-cardiac response data and the cardiac response data for the period deviate from trends of the extra-cardiac response information and the cardiac response information.

3. The system of claim 1, wherein the implantable static exertion sensor is configured to sense patient internal pressure and output a pressure signal responsive to patient static exertion, the pressure signal containing static exertion data, and wherein the processor is configured to execute stored program instructions to identify the steady state periods of physiological exertion based on the pressure signal.

4. The system of claim 1, further comprising an accelerometer configured to output a dynamic exertion signal responsive to patient movement, the dynamic exertion signal containing dynamic exertion data, wherein steady state periods of dynamic physiological exertion are further identified based on the dynamic exertion data.

5. The system of claim 4, wherein the processor is configured to execute stored program instructions to cause the system to classify one or more of the steady state periods of physiological exertion as either a static exertion period or a dynamic exertion period, wherein the one or more steady state periods are classified as static exertion if an increase in patient internal pressure is sensed without a corresponding increase in physical movement indicated by the dynamic exertion data and the one or more steady state periods are classified as dynamic exertion if the increase in patient internal pressure corresponds with the increase in physical movement indicated by the dynamic exertion data.

6. The system of claim 5, wherein the processor is configured to execute stored program instructions to cause the system to classify an episode of angina as stable angina, unstable angina, or vasospasm using the extra-cardiac response data, the cardiac response data, and the static or dynamic exertion period classification, wherein:
    the episode of angina is classified as stable angina if a corresponding period of exertion is classified as dynamic exertion and the physiological exertion-response data shows a non-proportional physiological response with respect to exertion intensity beyond an angina threshold, wherein below the angina threshold the physiological exertion-response data show a proportional physiological response with respect to exertion intensity;

the episode of angina is classified as unstable angina if the physiological exertion-response data shows the non-proportional physiological response with respect to exertion intensity with no angina threshold below which the physiological exertion-response data shows the proportional physiological response with respect to exertion intensity; and the episode of angina is classified as vasospasm if the corresponding period of exertion is classified as static exertion and the physiological exertion-response data shows the non-proportional physiological response with respect to exertion intensity beyond an angina threshold, wherein below the angina threshold the physiological exertion-response data shows the proportional physiological response with respect to exertion intensity.

7. The system of claim 1, wherein the processor is configured to execute stored program instructions to cause the system to modify a therapy based on a relatively high likelihood of ischemia being determined for a period of identified steady state physiological exertion.

8. The system of claim 1, wherein the patient-internal extra-cardiac parameter sensor is configured to sense data from which the processor can determine one or more of minute ventilation, tidal volume, pulmonary vascular pressure, core body temperature, venous oxygen saturation, and respiration rate.

9. The system of claim 1, wherein the patient-internal cardiac sensor is configured to sense data from which the processor can determine an electro-cardiac parameter and the processor is configured to execute stored program instructions to compare the electro-cardiac parameter to the cardiac response information to determine the myocardial ischemia likelihood, wherein the electro-cardiac parameter comprises one or more of heart rate, ST segment deviation, ST segment slope, FCC, PVC, AF %, QRS width, T-wave amplitude, T-wave polarity, and R-wave amplitude.

10. The system of claim 1, wherein the processor is configured to execute stored program instructions to cause the system to:

classify myocardial ischemia of one or more of the identified steady state periods of physiological exertion as exertion-related myocardial ischemia or non-exertion-related myocardial ischemia, wherein:

the myocardial ischemia is classified as exertion-related myocardial ischemia if the physiological exertion-response data sensed during the one or more steady state periods shows a non-proportional physiological response with respect to exertion intensity beyond a threshold, wherein below the threshold the physiological exertion-response data shows a proportional physiological response with respect to exertion intensity; and the myocardial ischemia is classified as non-exertion-related myocardial ischemia if the physiological exertion-response data sensed during the one or more steady state periods show the non-proportional physiological response with respect to exertion intensity with no threshold below which the physiological exertion-response data shows the proportional physiological response with respect to exertion intensity.

11. A system for characterizing myocardial ischemia, comprising:

an implantable static exertion sensor responsive to patient static exertion and configured to generate static exertion data;

an implantable extra-cardiac parameter sensor responsive to an extra-cardiac parameter and configured to output extra-cardiac response data;

an implantable cardiac parameter sensor responsive to a cardiac parameter and configured to output cardiac response data; and a processor configured to cause the system to:

identify steady state periods of physiological exertion based on the static exertion data and assign an exertion intensity level to each steady state period;

organize the respective extra-cardiac response and cardiac response data according to the assigned exertion intensity levels;

respectively compare the organized extra-cardiac and cardiac response data with extra-cardiac and cardiac response information associated with equivalent levels of physiological exertion intensity; and determine the likelihood that myocardial ischemia occurred during one or more of the steady state periods based on the comparison of the extra-cardiac and cardiac response data to the extra-cardiac and cardiac response information.

12. The system of claim 11, wherein the processor is configured to:

compute trends of the extra-cardiac response information and the cardiac response information; and determine the likelihood that myocardial ischemia occurred during one or more of the steady state periods based on a deviation of the extra-cardiac response and cardiac response data from the computed trends of the extra-cardiac response and cardiac response information, respectively.

13. The system of claim 11, wherein the processor is configured to determine the likelihood that myocardial ischemia occurred during one or more of the steady state periods as at least one of a relatively high likelihood or a relatively low likelihood that myocardial ischemia occurred during one or more of the steady state periods.

14. The system of claim 11, wherein the processor is configured to determine the likelihood that myocardial ischemia occurred during one or more of the steady state periods as at least one of a relatively high likelihood, a relatively moderate likelihood or a relatively low likelihood that myocardial ischemia occurred during one or more of the steady state periods.

15. The system of claim 11, wherein the processor, in determining the likelihood that myocardial ischemia occurred during one or more of the steady state periods, is further configured to determine normalcy of the extra-cardiac response data and cardiac response data for each steady state period based on the comparison of the extra-cardiac and cardiac response data to the extra-cardiac and cardiac response information.

16. The system of claim 11, wherein:

the likelihood that myocardial ischemia occurred during a steady state period of the identified steady state periods is determined by the processor to be relatively high if both the extra-cardiac response data and the cardiac response data for the steady state period deviate from trends of the extra-cardiac response information and the cardiac response information;

the likelihood that myocardial ischemia occurred during the steady state period is determined by the processor to be relatively moderate if only one of the extra-cardiac response data and the cardiac response data for the steady state period deviates from trends of the extra-cardiac response information and the cardiac response information; and the likelihood that myocardial ischemia occurred during the steady state period is determined by the processor to be relatively low if neither of the extra-cardiac response data and the cardiac response data for the steady state period deviates from trends of the extra-cardiac response information and the cardiac response information.

17. The system of claim 11, wherein the implantable static exertion sensor is configured to sense patient internal pressure and output a pressure signal responsive to patient static exertion, and wherein the processor is configured to identify the steady state periods of physiological exertion based on the pressure signal.

18. The system of claim 11, further comprising a sensor configured to output dynamic exertion data responsive to patient movement, wherein steady state periods of dynamic physiological exertion are further identified based on the dynamic exertion data.

19. The system of claim 18, wherein the processor is configured to cause the system to classify one or more of the steady state periods of physiological exertion as either a static exertion period or a dynamic exertion period, wherein the one or more steady state periods are classified as static exertion if an increase in patient internal pressure is sensed without a corresponding increase in physical movement indicated by the dynamic exertion data and the one or more steady state periods are classified as dynamic exertion if the increase in patient internal pressure corresponds with the increase in physical movement indicated by the dynamic exertion data.

20. The system of claim 11, further comprising a sensor configured to output dynamic exertion data responsive to patient movement, wherein the processor is configured to cause the system to:
classify one or more of the steady state periods of physiological exertion as either a static exertion period or a dynamic exertion period; and
classify an episode of angina as stable angina, unstable angina, or vasospasm using the extra-cardiac response data, the cardiac response data, and the static or dynamic exertion period classification.

21. The system of claim 11, wherein the processor is coupled to a memory configured to store an ischemia logbook, the processor configured to update the ischemia logbook in response to determining that myocardial ischemia likely occurred during one or more of the steady state periods.

22. A system for characterizing myocardial ischemia, comprising:
an implantable static exertion sensor configured to output an exertion signal responsive to patient static exertion, the exertion signal containing static exertion data;
at least one implantable physiological parameter sensor configured to output a physiological signal responsive to a physiological parameter, the physiological signal containing physiological exertion-response data;
an accelerometer configured to output a dynamic exertion signal responsive to patient movement, the dynamic exertion signal containing dynamic exertion data;
memory; and
a processor configured to execute program instructions stored in memory to cause the system to:
identify steady state periods of physiological exertion based on the static exertion data and assign one of a plurality of exertion intensity levels to each of the steady state periods;
organize the physiological exertion-response data according to the assigned exertion intensity levels of the identified steady state periods of physiological exertion during which the physiological exertion-response data was respectively output;
compare the physiological exertion-response data with stored physiological response information associated with equivalent levels of physiological exertion intensity of the steady state periods to which the physiological exertion-response data is organized; and
determine the likelihood that myocardial ischemia occurred during one or more of the periods based on the comparison of the physiological response information to the physiological exertion-response data;
wherein:
steady state periods of dynamic physiological exertion are further identified based on the dynamic exertion data; and
the processor is configured to execute stored program instructions to cause the system to classify one or more of the steady state periods of physiological exertion as either a static exertion period or a dynamic exertion period, wherein the one or more steady state periods are classified as static exertion if an increase in patient internal pressure is sensed without a corresponding increase in physical movement indicated by the dynamic exertion data and the one or more steady state periods are classified as dynamic exertion if the increase in patient internal pressure corresponds with the increase in physical movement indicated by the dynamic exertion data.

23. The system of claim 22, wherein the implantable static exertion sensor is configured to sense patient internal pressure and output a pressure signal responsive to patient static exertion, the pressure signal containing static exertion data, and wherein the processor is configured to execute stored program instructions to identify the steady state periods of physiological exertion based on the pressure signal.

24. The system of claim 22, wherein the processor is configured to execute stored program instructions to cause the system to classify an episode of angina as stable angina, unstable angina, or vasospasm using the extra-cardiac response data, the cardiac response data, and the static or dynamic exertion period classification, wherein:
the episode of angina is classified as stable angina if a corresponding period of exertion is classified as dynamic exertion and the physiological exertion-response data shows a non-proportional physiological response with respect to exertion intensity beyond an angina threshold, wherein below the angina threshold the physiological exertion-response data show a proportional physiological response with respect to exertion intensity;
the episode of angina is classified as unstable angina if the physiological exertion-response data shows the non-proportional physiological response with respect to exertion intensity with no angina threshold below which the physiological exertion-response data shows the proportional physiological response with respect to exertion intensity; and
the episode of angina is classified as vasospasm if the corresponding period of exertion is classified as static exertion and the physiological exertion-response data shows the non-proportional physiological response with respect to exertion intensity beyond an angina threshold, wherein below the angina threshold the physiological exertion-response data shows the proportional physiological response with respect to exertion intensity.

25. The system of claim 22, wherein the processor is configured to execute stored program instructions to cause the system to modify a therapy based on a relatively high likelihood of ischemia being determined for a period of identified steady state physiological exertion.

26. The system of claim 22, wherein the patient-internal extra-cardiac parameter sensor is configured to sense data from which the processor can determine one or more of minute ventilation, tidal volume, pulmonary vascular pressure, core body temperature, venous oxygen saturation, and respiration rate.

27. The system of claim 22, wherein the patient-internal cardiac sensor is configured to sense data from which the processor can determine an electro-cardiac parameter and the processor is configured to execute stored program instructions to compare the electro-cardiac parameter to the cardiac response information to determine the myocardial ischemia likelihood, wherein the electro-cardiac parameter comprises one or more of heart rate, ST segment deviation, ST segment slope, FCC, PVC, AF %, QRS width, T-wave amplitude, T-wave polarity, and R-wave amplitude.

28. The system of claim 22, wherein the processor is configured to execute stored program instructions to cause the system to:
classify myocardial ischemia of one or more of the identified steady state periods of physiological exertion as exertion-related myocardial ischemia or non-exertion-related myocardial ischemia, wherein:
the myocardial ischemia is classified as exertion-related myocardial ischemia if the physiological exertion-response data sensed during the one or more steady state periods shows a non-proportional physiological response with respect to exertion intensity beyond a threshold, wherein below the threshold the physiological exertion-response data shows a proportional physiological response with respect to exertion intensity; and
the myocardial ischemia is classified as non-exertion-related myocardial ischemia if the physiological exertion-response data sensed during the one or more steady state periods show the non-proportional physiological response with respect to exertion intensity with no threshold below which the physiological exertion-response data shows the proportional physiological response with respect to exertion intensity.

* * * * *